(12) United States Patent
Moehle et al.

(10) Patent No.: US 9,492,634 B2
(45) Date of Patent: Nov. 15, 2016

(54) CATHETER INCLUDING ARCUATE TRANSITION REGION

(75) Inventors: Ryan T. Moehle, Salt Lake City, UT (US); Ryan C. Patterson, Farmington, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 731 days.

(21) Appl. No.: 11/732,030

(22) Filed: Apr. 2, 2007

(65) Prior Publication Data

US 2007/0233042 A1   Oct. 4, 2007

Related U.S. Application Data

(60) Provisional application No. 60/744,094, filed on Mar. 31, 2006.

(51) Int. Cl.
| | | |
|---|---|---|
| *A61M 25/00* | (2006.01) | |
| *A61M 5/158* | (2006.01) | |
| *A61M 1/36* | (2006.01) | |

(52) U.S. Cl.
CPC ....... *A61M 25/0041* (2013.01); *A61M 1/3659* (2014.02); *A61M 1/3661* (2014.02); *A61M 5/1582* (2013.01); *A61M 25/007* (2013.01); *A61M 25/0021* (2013.01); *A61M 25/0023* (2013.01); *A61M 25/0029* (2013.01); *A61M 25/0068* (2013.01); *A61M 2025/0031* (2013.01); *A61M 2025/0037* (2013.01)

(58) Field of Classification Search
CPC ............ A61M 2025/0031; A61M 2025/0037; A61M 25/0041; A61M 25/0068

USPC .............. 604/523, 43, 93.01, 284, 533, 534, 604/4.01, 6.16
See application file for complete search history.

(56) References Cited

U.S. PATENT DOCUMENTS

| | | | |
|---|---|---|---|
| 256,590 | A | 4/1882 | Pfarre |
| 2,175,726 | A | 10/1939 | Gebauer |
| 2,590,895 | A | 4/1952 | Scarpellino |
| 2,910,981 | A | 11/1959 | Wilson et al. |
| 3,055,361 | A | 9/1962 | Ballard |
| 3,256,885 | A | 6/1966 | Higgins et al. |
| 3,434,691 | A | 3/1969 | Hamilton |
| 3,612,038 | A | 10/1971 | Halligan |
| 3,634,924 | A | 1/1972 | Blake et al. |
| 3,677,243 | A | 7/1972 | Nerz |
| 3,720,210 | A | 3/1973 | Diettrich |

(Continued)

FOREIGN PATENT DOCUMENTS

| | | |
|---|---|---|
| CA | 1092927 | 1/1981 |
| CA | 1150122 | 7/1983 |

(Continued)

OTHER PUBLICATIONS

PCT Written Opinion of the International Searching Authority; International Application No. PCT/US20074/008148. European Patent Office.

(Continued)

*Primary Examiner* — Emily Schmidt
(74) *Attorney, Agent, or Firm* — Rutan & Tucker, LLP

(57) ABSTRACT

A catheter, with one or more lumens, having a first portion and a second portion and an arcuate transition region extending between the first portion and the second portion. The first portion is nonparallel to the second portion.

17 Claims, 14 Drawing Sheets

(56) References Cited

U.S. PATENT DOCUMENTS

| | | |
|---|---|---|
| 3,812,851 A | 5/1974 | Rodriguez |
| 3,890,977 A | 6/1975 | Wilson |
| 3,921,631 A | 11/1975 | Thompson |
| 3,935,857 A | 2/1976 | Co |
| 3,942,528 A | 3/1976 | Loeser |
| 3,964,488 A | 6/1976 | Ring et al. |
| 3,983,203 A | 9/1976 | Corbett |
| 4,016,879 A | 4/1977 | Mellor |
| 4,020,829 A | 5/1977 | Willson et al. |
| 4,027,659 A | 6/1977 | Slingluff |
| 4,027,668 A | 6/1977 | Dunn |
| 4,033,331 A | 7/1977 | Guss et al. |
| 4,079,737 A | 3/1978 | Miller |
| 4,099,528 A | 7/1978 | Sorenson et al. |
| 4,117,836 A | 10/1978 | Erikson et al. |
| 4,134,402 A | 1/1979 | Mahurkar |
| 4,180,068 A | 12/1979 | Jacobsen et al. |
| 4,202,332 A | 5/1980 | Tersteegen et al. |
| 4,203,436 A | 5/1980 | Grimsrud |
| 4,217,895 A | 8/1980 | Sagae et al. |
| 4,220,813 A | 9/1980 | Kyle |
| 4,220,814 A | 9/1980 | Kyle et al. |
| 4,250,880 A | 2/1981 | Gordon |
| 4,270,535 A | 6/1981 | Bogue et al. |
| 4,292,976 A | 10/1981 | Banka |
| 4,300,550 A | 11/1981 | Gandi et al. |
| 4,306,562 A | 12/1981 | Osborne |
| 4,311,152 A | 1/1982 | Modes et al. |
| 4,352,354 A | 10/1982 | Ujihara et al. |
| 4,352,951 A | 10/1982 | Kyle |
| 4,385,631 A | 5/1983 | Uthmann et al. |
| 4,392,855 A | 7/1983 | Oreopoulos et al. |
| 4,402,685 A | 9/1983 | Buhler et al. |
| 4,403,983 A | 9/1983 | Edelman et al. |
| 4,405,313 A | 9/1983 | Sisley et al. |
| 4,417,888 A | 11/1983 | Cosentino et al. |
| D272,651 S | 2/1984 | Mahurkar |
| 4,451,252 A | 5/1984 | Martin et al. |
| 4,451,256 A | 5/1984 | Weikl et al. |
| 4,471,778 A | 9/1984 | Toye |
| 4,493,696 A | 1/1985 | Uldall et al. |
| 4,508,535 A | 4/1985 | Joh et al. |
| 4,531,933 A | 7/1985 | Norton et al. |
| 4,543,087 A | 9/1985 | Sommercorn et al. |
| 4,549,879 A | 10/1985 | Groshong et al. |
| 4,557,261 A | 12/1985 | Rugheimer et al. |
| 4,563,180 A | 1/1986 | Jervis et al. |
| 4,568,329 A | 2/1986 | Mahurkar |
| 4,568,338 A | 2/1986 | Todd |
| 4,576,199 A | 3/1986 | Svensson et al. |
| 4,581,012 A | 4/1986 | Brown et al. |
| 4,583,968 A | 4/1986 | Mahurkar |
| 4,595,005 A | 6/1986 | Jinotti |
| 4,596,559 A | 6/1986 | Fleischhacker |
| 4,619,643 A | 10/1986 | Bai et al. |
| 4,623,327 A | 11/1986 | Mahurkar |
| 4,626,240 A | 12/1986 | Edelman et al. |
| 4,643,711 A | 2/1987 | Bates |
| 4,648,868 A | 3/1987 | Hardwick et al. |
| 4,668,221 A | 5/1987 | Luther |
| 4,671,796 A | 6/1987 | Groshong et al. |
| 4,675,004 A | 6/1987 | Hadford et al. |
| 4,681,564 A | 7/1987 | Landreneau |
| 4,681,570 A | 7/1987 | Dalton |
| 4,682,978 A | 7/1987 | Martin et al. |
| 4,687,471 A | 8/1987 | Twardowski et al. |
| 4,687,741 A | 8/1987 | Farrell et al. |
| 4,692,141 A | 9/1987 | Mahurkar |
| 4,694,838 A | 9/1987 | Wijayarthna et al. |
| 4,701,159 A | 10/1987 | Brown et al. |
| 4,701,166 A | 10/1987 | Groshong et al. |
| 4,735,620 A | 4/1988 | Ruiz |
| 4,738,667 A | 4/1988 | Galloway |
| 4,739,768 A | 4/1988 | Engelson |
| 4,772,268 A | 9/1988 | Bates |
| 4,772,269 A | 9/1988 | Twardowski et al. |
| 4,773,431 A | 9/1988 | Lodomirski |
| 4,784,639 A | 11/1988 | Patel |
| 4,789,000 A | 12/1988 | Aslanian |
| 4,790,809 A | 12/1988 | Kuntz |
| 4,795,439 A | 1/1989 | Guest ............................ 604/43 |
| 4,808,155 A | 2/1989 | Mahurkar |
| 4,808,156 A | 2/1989 | Dean |
| 4,820,349 A | 4/1989 | Saab |
| 4,822,345 A | 4/1989 | Danforth |
| 4,834,709 A | 5/1989 | Banning et al. |
| 4,842,582 A | 6/1989 | Mahurkar |
| 4,846,814 A | 7/1989 | Ruiz |
| 4,867,742 A | 9/1989 | Calderon |
| 4,883,058 A | 11/1989 | Ruiz |
| 4,895,561 A | 1/1990 | Mahurkar |
| 4,898,669 A | 2/1990 | Tesio et al. |
| 4,909,787 A | 3/1990 | Danforth |
| 4,935,004 A | 6/1990 | Cruz |
| 4,961,731 A | 10/1990 | Bodicky et al. |
| 4,961,809 A | 10/1990 | Martin et al. |
| 4,973,306 A | 11/1990 | Ruiz |
| 4,976,703 A | 12/1990 | Franetzki et al. |
| 4,981,477 A | 1/1991 | Schon et al. |
| 4,985,014 A | 1/1991 | Orejola |
| 5,016,640 A | 5/1991 | Ruiz |
| 5,041,083 A | 8/1991 | Tsuchida et al. |
| 5,041,107 A | 8/1991 | Heil, Jr. |
| 5,045,072 A | 9/1991 | Castillo et al. |
| 5,053,003 A | 10/1991 | Dadson et al. |
| 5,053,004 A | 10/1991 | Markel et al. |
| 5,053,023 A | 10/1991 | Martin et al. |
| 5,057,073 A | 10/1991 | Martin et al. |
| 5,058,595 A | 10/1991 | Kern |
| 5,084,024 A | 1/1992 | Skinner |
| 5,098,413 A | 3/1992 | Trudell et al. ................ 604/530 |
| 5,141,499 A | 8/1992 | Zappacosta |
| 5,156,592 A * | 10/1992 | Martin et al. .................... 604/43 |
| 5,171,216 A | 12/1992 | Dasse et al. |
| 5,171,227 A | 12/1992 | Twardowski et al. |
| 5,188,619 A | 2/1993 | Myers |
| 5,197,951 A | 3/1993 | Mahurkar |
| 5,209,723 A | 5/1993 | Twardowski et al. .......... 604/43 |
| 5,221,255 A | 6/1993 | Mahurkar et al. |
| 5,221,256 A | 6/1993 | Mahurkar |
| 5,292,305 A | 3/1994 | Boudewijn et al. |
| 5,306,263 A | 4/1994 | Voda |
| 5,318,588 A | 6/1994 | Horzewski et al. |
| 5,324,274 A | 6/1994 | Martin et al. |
| 5,327,905 A | 7/1994 | Avitall |
| 5,346,471 A | 9/1994 | Raulerson |
| 5,350,358 A | 9/1994 | Martin |
| 5,354,271 A | 10/1994 | Voda |
| 5,354,297 A | 10/1994 | Avitall |
| 5,358,479 A | 10/1994 | Wilson |
| 5,358,493 A | 10/1994 | Schweich, Jr. et al. |
| 5,374,245 A | 12/1994 | Mahurkar |
| 5,380,276 A * | 1/1995 | Miller et al. ..................... 604/28 |
| 5,395,316 A | 3/1995 | Martin et al. |
| 5,401,258 A | 3/1995 | Voda |
| 5,403,291 A | 4/1995 | Abrahamson |
| 5,405,320 A | 4/1995 | Twardowski et al. .......... 604/43 |
| 5,405,341 A | 4/1995 | Martin et al. |
| 5,445,625 A | 8/1995 | Voda |
| 5,507,995 A | 4/1996 | Schweich, Jr. et al. |
| 5,509,897 A | 4/1996 | Twardowski et al. .......... 604/43 |
| 5,509,902 A | 4/1996 | Raulerson |
| 5,569,182 A | 10/1996 | Twardowski et al. .......... 604/43 |
| 5,569,197 A | 10/1996 | Helmus et al. |
| 5,569,218 A | 10/1996 | Berg |
| 5,599,311 A | 2/1997 | Raulerson |
| 5,624,413 A | 4/1997 | Markel et al. |
| 5,650,759 A | 7/1997 | Hittman et al. |
| 5,685,867 A | 11/1997 | Twardowski et al. ......... 604/523 |
| 5,718,678 A | 2/1998 | Fleming, III |
| 5,718,692 A | 2/1998 | Schon et al. |
| 5,741,233 A | 4/1998 | Riddle et al. |
| 5,755,760 A | 5/1998 | Maguire et al. |
| 5,776,111 A | 7/1998 | Tesio et al. |

(56) References Cited

U.S. PATENT DOCUMENTS

| | | |
|---|---|---|
| 5,795,326 A | 8/1998 | Siman |
| 5,830,184 A | 11/1998 | Basta |
| 5,830,196 A | 11/1998 | Hicks |
| 5,868,700 A | 2/1999 | Voda |
| 5,885,259 A | 3/1999 | Berg |
| 5,897,537 A | 4/1999 | Berg et al. |
| 5,902,282 A | 5/1999 | Balbierz |
| 5,941,872 A | 8/1999 | Berg |
| 5,944,732 A | 8/1999 | Raulerson et al. |
| 5,947,953 A | 9/1999 | Ash et al. |
| 5,957,961 A | 9/1999 | Maguire et al. |
| 5,961,486 A | 10/1999 | Twardowski et al. ......... 604/43 |
| 5,968,009 A | 10/1999 | Siman |
| 5,989,206 A | 11/1999 | Prosl et al. |
| 5,989,213 A | 11/1999 | Maginot |
| 6,001,079 A | 12/1999 | Pourchez et al. |
| 6,002,955 A | 12/1999 | Willems et al. |
| 6,004,280 A | 12/1999 | Buck et al. |
| 6,024,693 A | 2/2000 | Schock et al. |
| 6,033,382 A | 3/2000 | Basta |
| 6,083,213 A | 7/2000 | Voda |
| 6,156,016 A | 12/2000 | Maginot |
| 6,190,349 B1 | 2/2001 | Ash et al. |
| 6,190,371 B1 | 2/2001 | Maginot et al. |
| 6,277,100 B1 | 8/2001 | Raulerson et al. |
| 6,280,423 B1 | 8/2001 | Davey et al. |
| 6,293,927 B1 | 9/2001 | McGuckin, Jr. |
| 6,342,120 B1 | 1/2002 | Basta |
| 6,356,790 B1 | 3/2002 | Maguire et al. |
| 6,475,195 B1 | 11/2002 | Voda |
| 6,475,207 B1 | 11/2002 | Maginot et al. |
| 6,533,763 B1 | 3/2003 | Schneiter |
| 6,551,281 B1 | 4/2003 | Raulerson et al. |
| 6,585,705 B1 | 7/2003 | Maginot et al. |
| 6,595,966 B2 | 7/2003 | Davey et al. |
| 6,595,983 B2 | 7/2003 | Voda |
| 6,620,118 B1 | 9/2003 | Prosl et al. |
| 6,638,242 B2 | 10/2003 | Wilson et al. ............... 604/43 |
| 6,682,519 B1 | 1/2004 | Schon |
| 6,695,832 B2 | 2/2004 | Schon et al. |
| 6,719,749 B1 | 4/2004 | Schweikert et al. |
| 6,723,084 B1 | 4/2004 | Maginot et al. |
| D489,452 S | 5/2004 | Schweikert |
| 6,730,096 B2 | 5/2004 | Basta |
| D491,265 S | 6/2004 | Schweikert |
| 6,743,218 B2 | 6/2004 | Maginot et al. |
| 6,749,580 B2 | 6/2004 | Work et al. |
| 6,796,991 B2 | 9/2004 | Nardeo |
| D498,299 S | 11/2004 | Schweikert |
| 6,814,718 B2 | 11/2004 | McGuckin, Jr. et al. |
| 6,823,617 B2 | 11/2004 | Schweikert |
| 6,858,019 B2 * | 2/2005 | McGuckin et al. ........... 604/43 |
| 6,881,211 B2 * | 4/2005 | Schweikert et al. ......... 604/544 |
| D505,202 S | 5/2005 | Chesnin |
| 6,911,014 B2 | 6/2005 | Wentling et al. |
| 6,916,051 B2 | 7/2005 | Fisher |
| 6,926,669 B1 | 8/2005 | Stewart et al. |
| 6,926,721 B2 | 8/2005 | Basta |
| 6,939,328 B2 | 9/2005 | Raulerson |
| 6,969,381 B2 | 11/2005 | Voorhees |
| 6,986,752 B2 | 1/2006 | McGuckin, Jr. et al. |
| 6,991,625 B1 | 1/2006 | Gately et al. |
| D515,211 S | 2/2006 | Chesnin |
| 7,008,412 B2 | 3/2006 | Maginot |
| 7,011,645 B2 | 3/2006 | McGuckin, Jr. et al. |
| 7,018,374 B2 | 3/2006 | Schon et al. |
| 7,066,925 B2 | 6/2006 | Gately et al. |
| D525,359 S | 7/2006 | Stephens |
| 7,074,213 B2 | 7/2006 | McGuckin, Jr. et al. |
| 7,077,829 B2 | 7/2006 | McGuckin, Jr. et al. |
| D530,420 S | 10/2006 | Chesnin |
| 7,115,134 B2 | 10/2006 | Chambers |
| 7,163,531 B2 | 1/2007 | Seese et al. |
| 7,172,571 B2 | 2/2007 | Moskowitz et al. |
| 7,220,246 B2 | 5/2007 | Raulerson et al. |
| 7,223,263 B1 | 5/2007 | Seno |
| D544,600 S | 6/2007 | Wentling |
| D546,446 S | 7/2007 | Chesnin |
| 7,261,708 B2 | 8/2007 | Raulerson |
| 7,393,339 B2 | 7/2008 | Zawacki et al. |
| 7,494,478 B2 | 2/2009 | Itou et al. |
| 7,695,450 B1 | 4/2010 | Twardowski et al. |
| 7,799,013 B2 | 9/2010 | Gandras |
| 7,867,218 B1 | 1/2011 | Voda |
| 7,976,518 B2 | 7/2011 | Shaughnessy et al. |
| 8,021,321 B2 | 9/2011 | Zawacki |
| 8,029,457 B2 | 10/2011 | Ash et al. |
| 8,066,660 B2 | 11/2011 | Gregersen et al. |
| 8,092,415 B2 | 1/2012 | Moehle |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,323,227 B2 | 12/2012 | Hamatake et al. |
| 8,409,191 B2 | 4/2013 | Avitall et al. |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,827,943 B2 | 9/2014 | Angheloiu et al. |
| 8,876,754 B2 | 11/2014 | Ranchod et al. |
| 8,894,601 B2 | 11/2014 | Moehle et al. |
| 8,992,454 B2 | 3/2015 | Anand |
| 9,126,011 B2 | 9/2015 | Ash et al. |
| 9,131,956 B2 | 9/2015 | Shaughnessy et al. |
| 9,155,860 B2 | 10/2015 | Ash et al. |
| 9,174,019 B2 | 11/2015 | Gregersen |
| 9,233,200 B2 | 1/2016 | Gregersen et al. |
| 2002/0032411 A1 | 3/2002 | Basta |
| 2002/0091362 A1 | 7/2002 | Maginot et al. |
| 2003/0036698 A1 | 2/2003 | Kohler et al. |
| 2003/0066218 A1 | 4/2003 | Schweikert |
| 2003/0093027 A1 | 5/2003 | McGuckin et al. |
| 2003/0093029 A1 | 5/2003 | McGuckin et al. |
| 2003/0114832 A1 | 6/2003 | Kohler et al. |
| 2003/0144623 A1 * | 7/2003 | Heath et al. ................ 604/4.01 |
| 2004/0015151 A1 | 1/2004 | Chambers |
| 2004/0034324 A1 | 2/2004 | Seese et al. |
| 2004/0034333 A1 | 2/2004 | Seese et al. |
| 2004/0054321 A1 | 3/2004 | Schon et al. |
| 2004/0059314 A1 | 3/2004 | Schon et al. |
| 2004/0075198 A1 | 4/2004 | Schweikert et al. |
| 2004/0092863 A1 | 5/2004 | Raulerson et al. |
| 2004/0097903 A1 | 5/2004 | Raulerson |
| 2004/0122416 A1 | 6/2004 | Schweikert et al. |
| 2004/0186461 A1 | 9/2004 | DiMatteo |
| 2004/0193098 A1 | 9/2004 | Wentling et al. |
| 2004/0195131 A1 | 10/2004 | Spolidoro |
| 2004/0249349 A1 | 12/2004 | Wentling |
| 2005/0000844 A1 | 1/2005 | Schweikert |
| 2005/0015007 A1 | 1/2005 | Itou et al. |
| 2005/0038453 A1 | 2/2005 | Raulerson |
| 2005/0043684 A1 | 2/2005 | Basta et al. |
| 2005/0049572 A1 | 3/2005 | Schweikert et al. |
| 2005/0049628 A1 | 3/2005 | Schweikert et al. |
| 2005/0054990 A1 | 3/2005 | Graft et al. |
| 2005/0085765 A1 | 4/2005 | Voorhees |
| 2005/0096580 A1 | 5/2005 | Moskowitz et al. |
| 2005/0096585 A1 | 5/2005 | Schon et al. |
| 2005/0096609 A1 | 5/2005 | Maginot et al. |
| 2005/0101903 A1 | 5/2005 | Kohler et al. |
| 2005/0107770 A1 | 5/2005 | Schweikert et al. |
| 2005/0113801 A1 | 5/2005 | Gandras ..................... 604/523 |
| 2005/0120523 A1 | 6/2005 | Schweikert |
| 2005/0124970 A1 | 6/2005 | Kunin et al. |
| 2005/0137527 A1 | 6/2005 | Kunin |
| 2005/0137580 A1 | 6/2005 | Raulerson et al. |
| 2005/0192545 A1 | 9/2005 | Voorhees et al. |
| 2005/0209583 A1 | 9/2005 | Powers et al. |
| 2005/0222593 A1 | 10/2005 | Markel et al. |
| 2005/0234369 A1 | 10/2005 | Voorhees |
| 2005/0245900 A1 * | 11/2005 | Ash ........................... 604/537 |
| 2005/0261665 A1 | 11/2005 | Voorhees |
| 2006/0004316 A1 | 1/2006 | Difiore et al. |

(56) References Cited

U.S. PATENT DOCUMENTS

| | | | |
|---|---|---|---|
| 2006/0004324 A1* | 1/2006 | Ruddell et al. | 604/29 |
| 2006/0015072 A1 | 1/2006 | Raulerson | |
| 2006/0015130 A1 | 1/2006 | Voorhees et al. | |
| 2006/0030827 A1 | 2/2006 | Raulerson et al. | |
| 2006/0047267 A1 | 3/2006 | Gately et al. | |
| 2006/0047268 A1 | 3/2006 | Stephens | 604/533 |
| 2006/0064072 A1 | 3/2006 | Gately et al. | |
| 2006/0095030 A1 | 5/2006 | Avitall et al. | |
| 2006/0095062 A1 | 5/2006 | Stephens | |
| 2006/0184142 A1 | 8/2006 | Schon et al. | |
| 2006/0189959 A1 | 8/2006 | Schneiter | |
| 2006/0200111 A1 | 9/2006 | Moehle et al. | |
| 2006/0206094 A1 | 9/2006 | Chesnin et al. | |
| 2006/0253063 A1 | 11/2006 | Schweikert | |
| 2006/0271012 A1 | 11/2006 | Canaud et al. | |
| 2007/0043307 A1 | 2/2007 | Raulerson et al. | |
| 2007/0049960 A1 | 3/2007 | Stephens et al. | |
| 2007/0060866 A1 | 3/2007 | Raulerson et al. | |
| 2007/0073271 A1 | 3/2007 | Brucker et al. | |
| 2007/0135794 A1 | 6/2007 | Raulerson et al. | |
| 2007/0198047 A1 | 8/2007 | Schon et al. | |
| 2007/0219510 A1 | 9/2007 | Zinn et al. | |
| 2007/0225661 A1 | 9/2007 | Ash et al. | |
| 2007/0225682 A1 | 9/2007 | Ash et al. | |
| 2007/0225683 A1 | 9/2007 | Raulerson et al. | |
| 2007/0225684 A1 | 9/2007 | Wentling et al. | |
| 2007/0233017 A1 | 10/2007 | Zinn et al. | |
| 2007/0233018 A1 | 10/2007 | Bizup et al. | |
| 2008/0021417 A1 | 1/2008 | Zawacki et al. | |
| 2008/0039774 A1 | 2/2008 | Zawacki et al. | |
| 2008/0045886 A1 | 2/2008 | Hobbs et al. | |
| 2008/0045894 A1 | 2/2008 | Perchik et al. | |
| 2008/0097339 A1 | 4/2008 | Ranchod et al. | |
| 2009/0018493 A1 | 1/2009 | Ash et al. | |
| 2014/0200524 A1 | 7/2014 | Wiley et al. | |

FOREIGN PATENT DOCUMENTS

| | | | |
|---|---|---|---|
| DE | 545218 | 2/1932 | |
| DE | 2627850 | 1/1977 | |
| DE | 2627851 | 1/1977 | |
| DE | 3736226 | 5/1989 | |
| DK | 146777 | 10/1977 | |
| EP | 0036642 | 9/1981 | |
| EP | 0081724 | 6/1983 | |
| EP | 0102342 A2 | 3/1984 | |
| EP | 0132344 | 1/1985 | |
| EP | 0242985 | 10/1987 | |
| EP | 256478 | 2/1988 | |
| EP | 0263645 | 4/1988 | |
| EP | 323738 | 7/1989 | |
| EP | 0386408 | 9/1990 | |
| EP | 386408 A1 * | 9/1990 | A61M 25/00 |
| ES | 2069287 | 6/1993 | |
| FR | 2529083 | 12/1983 | |
| GB | 2238724 | 6/1991 | |
| JP | 59034265 | 2/1984 | |
| JP | 63111833 | 5/1988 | |
| JP | 1058263 | 3/1989 | |
| JP | 1238872 | 9/1989 | |
| WO | WO 91/15255 | 10/1991 | |
| WO | WO-9212754 | 8/1992 | |
| WO | WO 93/21983 | 11/1993 | |
| WO | 9624399 A1 | 8/1996 | |
| WO | 9717102 | 5/1997 | |
| WO | 0023137 A1 | 4/2000 | |
| WO | 02/13899 A1 | 2/2002 | |
| WO | WO 02/30489 | 4/2002 | |
| WO | 03030960 A2 | 4/2003 | |

OTHER PUBLICATIONS

Vas-Cath; Niagara, Dual Lumen Catheter Instructions for Use; Jun. 1997; Canada.
Vas-Cath; Opti-Flow and Soft-Cell; Dual Lumen Catheter Straight and Pre-Curved (PC) Catheters, with and without VitaCuff; Jun. 16, 1997.
Bard Access Systems; Power Picc The Universal Picc, Polyurethane PICC with Safety Excalibur Introducer System Instructions for Use; Jul. 2003.
Bard Access Systems; PowerPicc, The Universal Picc, Polyurethane Radiology Catheters with Microintroducer Set Instructions for Use; Nov. 2003.
Bard; 135cm Guidewire, Instructions for Use; Mar. 2002, excerpt.
Bard Access Systems; HemoSplit Long-Term Hemodialysis Catheter, Instructions for Use; Apr. 2003.
McIntosh, Berry, Thompson, and Durham; Double Lumen Catheter for Use with Artificial Kidney; J.A.M.A.; Feb. 21, 1959; 137/835-138/836.
Medcomp; Effective Solutions for Vascular Access; Product Line; Apr. 2006; Rev. D.
Cournand et al. "Double Lumen Catheter for Intravenous and Intracardiac Blood Sampling and Pressure Recording." Proceedings of the Society for Experimental Biology and Medicine, vol. 60, pp. 73, 1994.
Cook Critical Care; Cook TPN Pre-Cut Double Lumen Catheters with Off-Set Tips; A000053 1982.
Raja et al. "Comparison of Double Lumen Subclavian with Single Lumen Catheter—One Year Experience." Trans American Society of Artificial Internal Organs, vol. XXX 1984.
Zuniga et al. "Hemodialisis: Accesso Vascular Con Cateter De Doble Lumen." Rev. Med. Chile; 117: pp. 991-996, 1989.
Vanherweghem et al. "Complications Related to Subclavian Catheters for Hemodialysis." American Journal of Nephrol 6, pp. 339-345, 1986.
Lally et al. "Use of Subclavian Venous Catheter for Short- and Long-term Hemodialysis in Children." Journal of Pediatric Surgery, vol. 44, No. 7, pp. 603-605, 1987.
Cheesbrough et al. "A Prospective Study of the Mechanisms of Infection Associated with Hemodialysis Catheters." The Journal of Infectious Diseases vol. 154, No. 4, pp. 579-589, 1986.
Ota et al. "A Completely New Poly(ether-urethane) Graft Ideal for Hemodialysis Blood Access." Trans Am Soc Artif Intern Organs, vol. XXXIII, pp. 129-135, 1987.
Scribner et al. "Evolution of the Technique of Home Parenteral Nutrition." Journal of Parenteral and Enteral Nutrition. vol. 3, No. 2, pp. 58-61, 1979.
Sanders et al. "Experience with Double Lumen Right Atrial Catheters." American Society of Parenteral and Enteral Nutrition, vol. 6, No. 2., pp. 95-99, 1982.
Shiley ©; Subclavian Cannulae product brochure, 1986.
Hickman, Robert O., et al., "A Review of Hemodialysis Catheters and Access Devices." Dialysis & Transplantation, vol. 16, No. 9, pp. 481 485, 1997.
Annest, Lon S et al. "Use of a Split-Sheath Vein Introducer for Subclavian Venipuncture in the Placement of Silicone Catheters for Chronic Venous Access." The American Journal of Surgery, vol. 144, pp. 367-369, 1982.
McDowell, Donald E., et al., "A Simplified technique for percutaneous insertion of permanenet vascular access catheters in patients requiring chronic hemodialysis." Section of Vascular Surgery, Department of Surgery, West Virginia University Medical Center, Morgantown, WV 26505.
Sims, Terran W., et al., "Successful Utilization of Subclavian Catheters for Hemodialysis and Apheresis Access", AANNT Journal, vol. 10, No. 6, 1993.
Uldall, P.R., et al., "A Subclavian Cannula for Temporary Vascular Access for Hemodialysis of Plasmapheresis." Dialysis & Transplantation, vol. 8, No. 10, p. 963, 1979.
Carbone, Vera, "Hemodialysis Using the PermCath Double Lumen Catheter." ANNA Journal, vol. 15, No. 3, pp. 171-173, 1988.
Bregman, Harold, et al., "Minimum Performance Standards for Double-Lumen Subclavian Cannulas for Hemodialysis." vol. 32, No. 1, 1986.
Vas-Cath; Soft-cell Permanent Dual Lumen Cannula with Dacron Cuff; Product details; 1988.

(56) References Cited

OTHER PUBLICATIONS

Vas-Cath; Instructions for use of Soft-cell Permanent Dual Lumen Catheter; May 25, 1998.
Saklayen, "Letters to the editor re: prolonged use of a Subclavian Catheter for Hemodialysis." Dialysis & Transplantation, Apr. 1998.
Quinton Instrument Co; Descriptions and Instructions for use of PermCath HemoCath Dual Lumen Catheter; 1984.
Vas-Cath; Permanent Dual Lumen Catheter for Vas-Cath; Advertisement; Contemporary Dialysis and Nephrology, May 1988.
Vas-Cath; The Vas-Cath Advantage: Temporary and Permanent Dual Lumen Catheters, Flexxicon® & Flexxicon® Blue brochure.
Vas-Cath; Temporary Vascular Access Products; Product Line; 1985.
Shiley; Subclavian Cannulae; Aug. 1986.
Medcomp; Hemodialysis Products; Product line.
Impra; Dual Lumen Subclavian Catheter; Information.
Cook Incorporated; Subclavian Double Lumen Hemodialysis Sets and Trays; U.S. Pat. No. 4,306,562.
Vas-Cath; Catheter Repair Kit CRK-1 with Titanium Replacement Connector; 1988.
Vas-Cath; Peritoneal Dialysis Catheters; Indications for use; 1988.
Vas-Cath; Instructions for use of Flexxicon Dual Lumen Catheters (DLC), Kits (DLK), Trays (DLT); 1988.
Vas-Cath; Vaccess 2000 Series Single Lumen Subclavian Cannulas (Central Venous Access/Hemodialysis). Brochure distributed by Vas-Cath.
Vas-Cath; Vaccess 2000 Series Single Lumen Subclavian Cannulas (Single Needle Hemodialysis); 1984.
Vas-Cath; Vaccess 1000 Series Single Lumen Femoral Cannulas (Hemodialysis); 1984.
Vas-Cath; For acute dialysis . . . Vas-Cath is accessible; Advertistement; 1987.
Vas-Cath; Flexxicon Dual Lumen Catheters. Instructions for Use distributed by Vas-Cath.
Quinton Instrument Company; Peritoneal Dialysis and Hemodialysis; Catalog.
Aubaniac, Robert. "L'injection intraveineuse sous-claviculaire: Avantages et technique." La Presse Medicale. 1952.
Cimochowski, George E., et al., "Superiority of the Internal Jugular over teh Subclavian Access for Temporary Dialysis." Nephron, vol. 54, No. 2, 1990.
Duffy, B. J. "The Clinical Use of Polyethylene Tubing for Intravenous Therapy." Annals of Surgery, vol. 136, No. 5, 1949.
Erben, Joseph, et al., "Experience with Routine use of Subclavian Vein Cannulation in Haemodialysis." Dialysis and Renal Transplantation, vol. 6, 1969.
Hoshal, Verne L., et al., "Fibrin Sleeve Formation on Indwelling Subclavian Central Venous Catheters." Archives of Surgery, vol. 102, 1971.
Ratcliffe, P.J. et al., "Massive Thrombosis around Subclavian Cannulas Used for Haemodialysis" The Lancet (Letters to the Editor), vol. 1, No. 8287, 1982.
Schillinger, F., et al., "Post Catheterisation Vein Stenosis in Haemodialysis: Comparative Angiographic Study of 50 Subclavian and 50 Internal Jugular Accesses", Nephrology Dialysis Transplantation, vol. 6, No. 10, 1991.
Shaldon, Stanley, et al., "Hemodialysis by Percutaneous Cathererisation of the Femoral Artery and Vein with Regional Heparinisation." The Lancet, vol. 2, 1961.
Twardowski, Zbylut J., "Chapter 57: Peritoneal Catheter Placement and Management." Suki and Massry's Therapy of Renal Diseases and Related Disorders, Third Edition.
Young, Warren, "Chapter 14: Elastic Stability". Roark's Formulas for Stress Strain 1989.
Vas-Cath; Accessories/Price List for Canadian Hospitals, Hemodialysis Products effecive May 1, 1982.
Vas-Cath; Vaccess 2 Double-Lumen Subclavian Cannula.
Vas-Cath; Single Lumen PTFE SubClavian/Femoral Cannulas, Sc-100; Advertisement.
Vas-Cath; Temporary Vascular Access Products.
Bregman, Harold, et al.,"The Double-Lumen Subclavian Cannula—A Unique Concept in Vascular Access". Dialysis & Transplantation, vol. 11, No. 12, pp. 1065-1070, 1982.
Vas-Cath; Vaccess 2000: Single Lumen Subclavian Cannulas, Instructions for Use—Central Venous Access.
Vas-Cath; Accessories/Price List.
Peters, Joseph L., et al., "Long-term venous access." British Journal of Hospital Medicine, 1984.
Berlyne, G.M., "Editorial: Hemodialysis versus the Newer Techniques." Nephron, vol. 27, No. 1, 1981.
Seldinger, Sven Irar, "Catheter Replacement of the Needle in Percutaneous Arteriography." Roentgen Diagnostic Department, Karolnska Sjukhuset, Stockholm, Sweden.
Shaldon, Stanley, et al., "New Developments with Artificial Kidney." British Medical Journal, London, Jun. 29, 1963.
Dialysis & Transplantation (A creative Age Publication); vol. 13, No. 8, Aug. 1984.
Pristave, Robert J., "Medicare Audits." Dialysis & Transplantation, vol. 12, No. 7, Jul. 1983.
Bricker, Catherine., "Psychosocial Implications of Nutrition Assessment for Adult Chronic Renal Failure Patients." Dialysis & Transplantation, vol. 11, No. 5, May 1982.
Dialysis & Transplantation (A creative Age Publication); vol. 11 No. 6,Jun. 1982.
Dialysis & Transplantation; vol. 11, No. 7, Jul. 1982.
Dialysis & Transplantation; vol. 11, No. Aug. 1982.
Dialysis & Transplantation; vol. 11, No. 9, Sep. 1982.
Dialysis & Transplantation; vol. 11, No. 11, Nov. 1982.
Dialysis & Transplantation; vol. 11, No. 12, Dec. 1982.
Dialysis & Transplantation; vol. 12, No. 1, Jan. 1983.
Dialysis & Transplantation; vol. 12, No. 2, Feb. 1983.
Dialysis & Transplantation; vol. 12, No. 3, Mar. 1983.
Dialysis & Transplantation; vol. 12, No. 4, Apr. 1983.
Dialysis & Transplantation; vol. 12, No. 5, May 1983.
Dialysis & Transplantation; vol. 12, No. 6, Jun. 1983.
Dialysis & Transplantation; vol. 12, No. 7, Jul. 1983.
Dialysis & Transplantation; vol. 12, No. 8, Aug. 1983.
Dialysis & Transplantation; vol. 12, No. 9, Sep. 1983.
Dialysis & Transplantation; vol. 13, No. 5, May 1984.
Dialysis & Transplantation; vol. 13, No. 6, Jun. 1984.
Dialysis & Transplantation; vol. 13, No. 7, Jul. 1984.
Dialysis & Transplantation; vol. 13, No. 9, Sep. 1984.
Dialysis & Transplantation; vol. 13, No. 10, Oct. 1984.
Dialysis & Transplantation; vol. 14, No. 3, Mar. 1985.
Dialysis & Transplantation; vol. 14, No. 5, May 1985.
Dialysis & Transplantation; vol. 13, No. 8, Aug. 1984.
Dialysis & Transplantation; vol. 17, No. 6, Jun. 1988.
Dunn, John, et al., "Centra venous dialysis access: Experience with a dual-lumen, silicone rubber catheter." Surgery, vol. 102, No. 5, Nov. 1987.
Twardowski, Zbylut J., "The Need for a 'Swan-Neck' Permantently Bent Arcuate Peritoneal Dialysis Catheter." Peritoneal Dialysis Bulletin, Oct.-Dec. 1985.
Vas-Cath; Soft-Cell Permanent Dual Lumen Catheter; Insertion Guide.
Quinton; PermCath and Pediatric PermCath Catheters; Instructions for Use.
Netter, Frank H.; A compilation of Paintings on the Normal and Pathologic Anatomy and Physiology, Embryology, and Diseases of the Heart; The Ciba Collection of Medical Illustrations, vol. 5.
Palmer, Russell A., "Treatment of Chronic Renal Failure by Prolonged Peritoneal Dialysis." The New England Journal of Medicine, vol. 274, No. 5, Feb. 3, 1966.
Palmer, Russell A, et al., "Prolonged Peritoneal Dialysis for Chronic Renal Failure," The Lancet, Mar. 28, 1964.
Vas-Cath; Confidential Training Manual and Marketing Support File for Vascular Access Catheters and Accessories for Dialysis; Revised Jan. 1989.
Bard; HemoGlide Long Term Hemodialysis Catheter. Instructions for Use for HemoGlide Straight and Precurved (PC) Catheters, with and without VitaCuff © Antimicrobial Cuff, 2002.
Vas-Cath; Vaccess 2000: Single Lumen Subclavian Cannulas, Instructions for Use—Single Needle Hemodialysis.

(56) References Cited

OTHER PUBLICATIONS

Vas-Cath, "Uldall™ SC-100 Means Quality" Advertisement, 1980.
Shiley © "Major Improvement. Major Advantage. Shiley's All-Silicone Subclavian Cannual." Brochure, 1980.
Vas-Cath, "Go for the Jugular" temporary catheter product advertisement, 1994.
Quinton et al. "Eight Months' Experience with Silastic-Teflon Bybass Cannulas," Department of Medicine and Surgery, Universityof Washington and the Quinton Instrument Company, 1961.
PCT/US2007/008148 filed Apr. 2, 2007 Search Report dated Aug. 28, 2007.

* cited by examiner

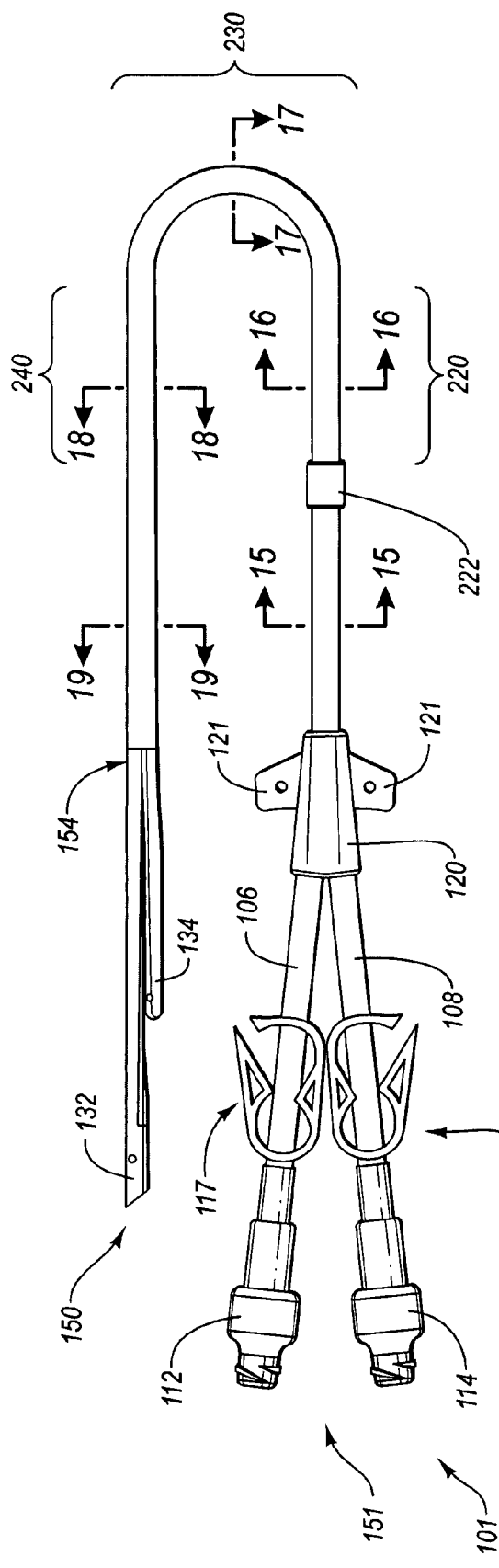
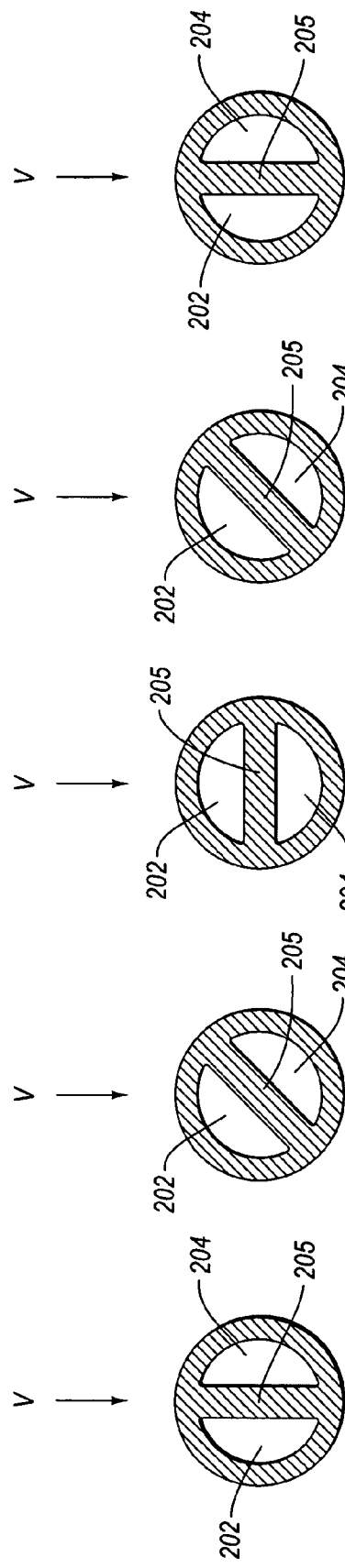
FIG. 14
FIG. 15 FIG. 16 FIG. 17 FIG. 18 FIG. 19

CATHETER INCLUDING ARCUATE TRANSITION REGION

CROSS-REFERENCE TO RELATED APPLICATION

This application claims the benefit of U.S. Provisional Application No. 60/744,094, entitled "CATHETER INCLUDING ARCUATE TRANSITION REGION AND/OR AT LEAST ONE TRANSFORMATION REGION," filed Mar. 31, 2006, which is incorporated herein by reference in its entirety.

BACKGROUND

Embodiments described herein are related to a catheter suitable for insertion into a vein of a patient. A catheter is a conduit or tube that is inserted into a body cavity, duct or blood vessel. Catheters may be used for various processes in which bodily fluids, medicaments, or other solutions are introduced and removed from the body, such as perfusion, infusion, apheresis, hemodialysis, chemotherapy, or other processes known in the art.

SUMMARY

In one embodiment, a catheter includes a catheter body extending between a distal end and a proximal end and defining at least one lumen, a first portion and a second portion, and an arcuate transition region extending between the first portion and the second portion, such that the arcuate transition region is configured to be at or near an insertion site into the body of a patient, the arcuate transition region including an exterior angle greater than 180 degrees.

In another embodiment, a catheter includes a catheter body extending between a distal end and a proximal end and defining two lumens, a first portion and a second portion, and an arcuate transition region extending between the first portion and the second portion; wherein at least a majority of the first portion is configured to be disposed outside the body of a patient and, wherein at least a segment of the second portion has a length suitable for insertion inside the body of the patient, and wherein the exterior angle between a central axis of the first portion and a central axis of the second portion is greater than 180 degrees.

In another embodiment, a catheter includes a catheter body extending between a distal end and a proximal end and defining at least two lumens, a first portion and a second portion, and an arcuate transition region extending between the first portion and the second portion, wherein the arcuate transition region includes an exterior angle greater than 180 degrees, at least one transformation region between the first portion and the second portion within which the position of a septum dividing the two lumens at least partially changes, and a separation angle formed between a central axis of the first portion and a central axis of the second portion, wherein the separation angle is no more than about 90 degrees.

BRIEF DESCRIPTION OF THE DRAWINGS

Understanding that drawings depict only typical embodiments of the disclosure and are not therefore to be considered to be limiting of its scope, the present embodiments will be described and explained with additional specificity and detail through the use of the accompanying drawings as listed below.

FIG. 14 shows a top elevation view of one embodiment of a catheter including a plurality of transformation regions.

FIGS. 15-19 show different cross-sectional views of one embodiment of the catheter shown in FIG. 14.

DETAILED DESCRIPTION OF THE EXEMPLARY EMBODIMENTS

Generally, one aspect of the instant disclosure relates to a catheter including an arcuate transition region. Another aspect of the instant disclosure relates to a transformation region within which an orientation of at least one lumen comprising the catheter changes. In addition, a catheter including an arcuate transition region and/or at least one transformation region may include at least one proximal connection structure for facilitating fluid communication with an associated lumen of the catheter and at least one distal leg or portion.

The relative term "distal" refers to those portions of a catheter and those portions of components of the catheter that are nearer, relatively, to an insertion end of the catheter, that is, the end of the catheter that is inserted into an area of a patient's body, such as a blood vessel. In addition, the relative term "proximal" refers to those portions of a catheter and those portions of components of the catheter that are farther, relatively, from the insertion end of the catheter. In one aspect of the instant disclosure, a distal portion of the catheter may cross over or intersect with a proximal portion of the catheter. In addition, optionally, a selected exterior angle may be formed between a central axis of a first portion of the catheter and a central axis of a second portion of the catheter.

As mentioned above, one aspect of the instant disclosure relates to a catheter including an arcuate transition region. Such a catheter may be used for various processes in which bodily fluids, medicaments, or other solutions are introduced and removed from the body, such as perfusion, infusion, apheresis, hemodialysis, chemotherapy, or other processes known in the art. For example, a catheter may be utilized for a hemodialysis catheterization, such as the internal jugular vein catheterization. However, it should be understood by one skilled in the art based on this disclosure, that a catheter can be structured (e.g., increasing or decreasing the catheter size and/or shape, changing a number of lumens defined by the catheter, selecting materials comprising a catheter, etc.) such that the catheter can be beneficially used for a selected medical application in which fluids are introduced and/or removed from the body.

Figure 1:
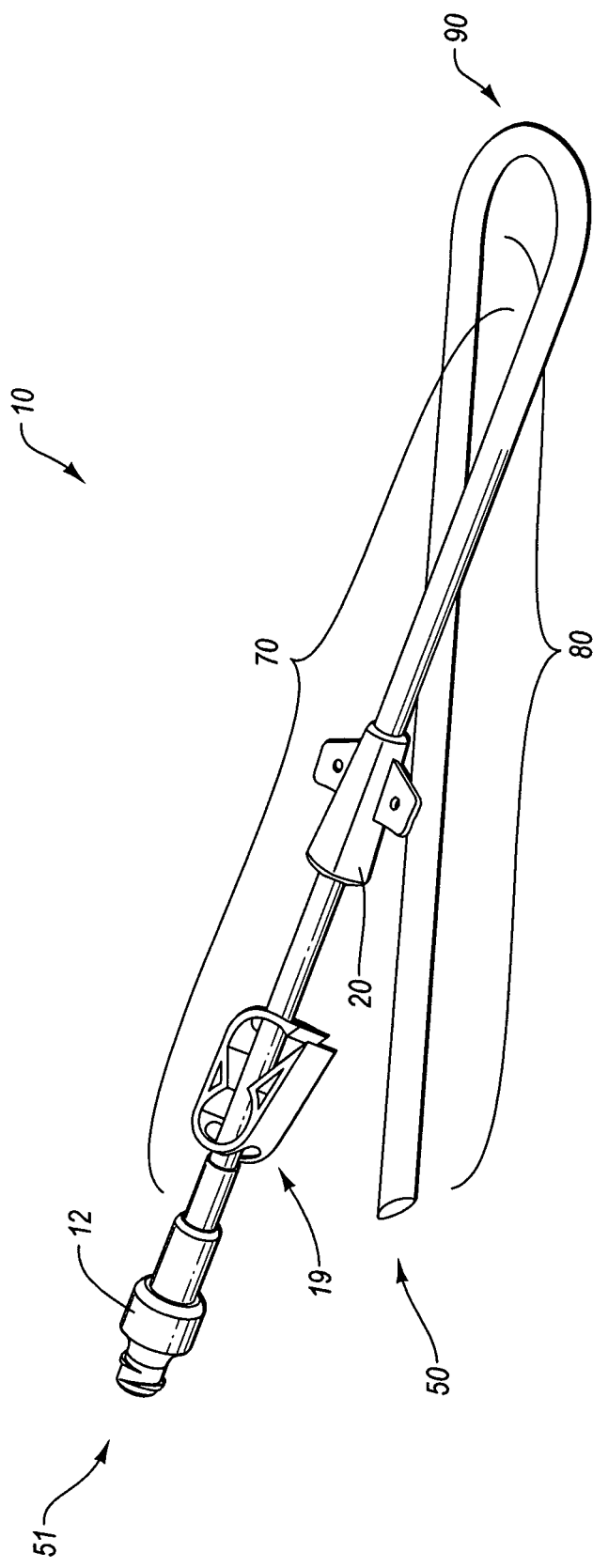
FIG. 1 shows a perspective view of one embodiment of a catheter including an arcuate transition region.

For example, FIG. 1 shows a perspective view of one embodiment of a catheter 10 encompassed by the instant disclosure. As shown in FIG. 1, the catheter 10 extends between a distal end 50 for insertion into a patient and a proximal end 51. As known in the art, optionally, catheter 10 may include a stabilizing cuff affixed to an outer portion of the body of the catheter at a selected longitudinal position such that the cuff will be ultimately positioned within a subcutaneous tunnel formed in the patient. The catheter 10 may also optionally include a hub structure 20 and a clamp device 19. In one embodiment, as discussed in greater detail below, proximal end 51 may include a connector 12 configured for connection to a device used to introduce or remove fluid from at least one lumen of the catheter 10. In further detail, catheter 10 comprises a catheter body including a first portion 70, a second portion 80, and an arcuate transition region 90 extending between the first portion 70 and the second portion 80.

In one embodiment, the arcuate transition region 90 is configured to be at or near an insertion site into the body of a patient. The arcuate transition region 90 near the insertion site indicates that it is located at a position adjacent or close to the location where the catheter enters the body of a patient. The arcuate transition region near the insertion site can be located adjacent to the insertion site on either the interior of the body or the exterior of the body. For example, in one exemplary embodiment the arcuate transition region near the insertion site may be disposed within the body at a location within 5 cm of the insertion site. One having skill in the art would appreciate that "near the insertion site" is a relative term and may depend, in part, on the size of the arcuate region and the catheter used.

In one embodiment, at least a majority of the first portion 70 is configured to be disposed outside the body of a patient and at least a segment of the second portion 70 has a length suitable for insertion inside the body of the patient. In yet another embodiment, the distal end 50 may include a non-helical terminus. In one embodiment, catheter 10 may comprise one or more lumens.

Figure 2:
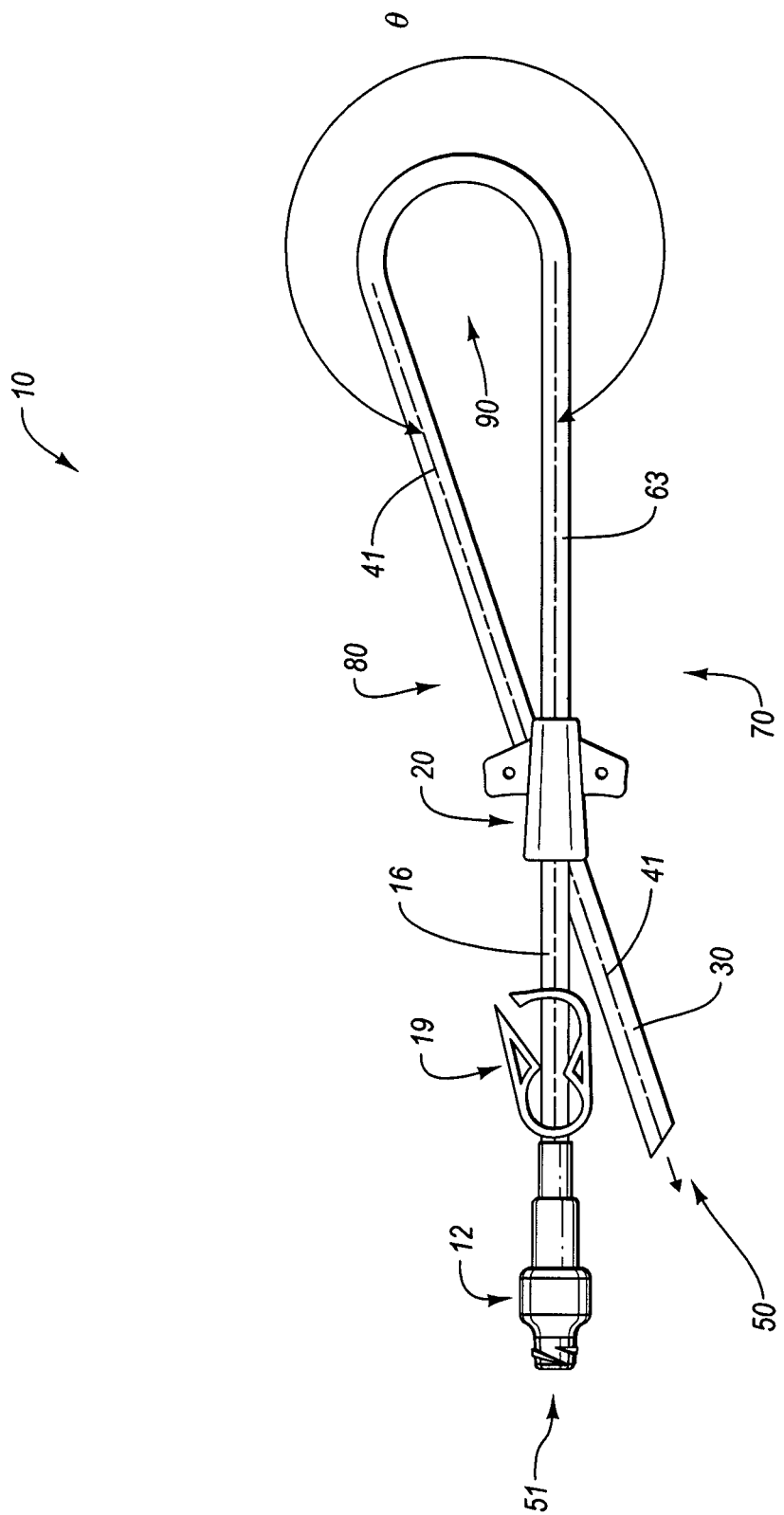
FIG. 2 shows a bottom elevation view of the catheter shown in FIG. 1.

Generally, the instant disclosure contemplates that arcuate transition region 90 may be structured so that first portion 70 is nonparallel with respect to second portion 80. FIG. 2 shows a bottom elevation view of catheter 10 that shows first portion 70 in relation to second portion 80. More particularly, as shown in FIG. 2, a selected exterior angle may be formed between the first portion 70 and the second portion 80, when the catheter 10 is in a substantially unstressed state.

In one embodiment, an exterior angle formed between the first portion 70 and the second portion 80 may exceed 180°. For example, the angle formed between the first portion 70 and the second portion 80 may range from approximately 180-190°, 190-200°, 200-210°, 210-220°, 220-230°, 230-240°, 240-250°, 250-260°, and 260-270°. In yet another embodiment, an exterior angle formed between the first portion 70 and the second portion 80 may be less than 180°. For example, the angle formed between the first portion 70 and the second portion 80 may range from approximately 0-10°, 10-20°, 20-30°, 30-40°, 40-50°, 50-60°, 60-70°, 70-80°, 80-90°, 100-110°, 110-120°, 120-130°, 130-140°, 140-150°, 150-160°, 160-170°, and 170-180°. More particularly, an exterior angle between the first portion 70 and the second portion 80 may be about 225°.

The instant disclosure generally contemplates, without limitation, that the exterior angle may be measured between any surfaces of the first portion 70 and/or the second portion 80. Variations (i.e., increases or decreases) in the magnitude of a measurement of an exterior angle due to a thickness or size of the first portion 70 and/or the second portion 80 are encompassed by the above-discussed exterior angle embodiments. One of ordinary skill in the art will appreciate that at least a portion of arcuate transition region 90 may form a generally circular arc. The instant disclosure further contemplates that, in other embodiments, at least a portion of arcuate transition region 90 may comprise at least one of the following: a generally elliptical arc, a generally parabolic curve, and a generally concave curve.

In one embodiment, an exterior angle may be measured between a central axis of the first portion 70 and a central axis of the second portion 80. For example, angle $\theta$ is shown in FIG. 2 extending between a central axis 63 extending along first portion 70 (e.g., along a centroid of a cross-sectional area of the first portion 70) and a central axis 41 extending along second portion 80 (e.g., along a centroid of a cross-sectional area of the second portion 80). Thus, a selected angle $\theta$ may be formed between central axis 63 of first portion 70 and central axis 41 of second portion 80, when arcuate transition portion 90 of catheter 10 is in a substantially unstressed state. In one embodiment, as shown in FIG. 2, exterior angle $\theta$ may exceed 180°. In one embodiment, exterior angle $\theta$ may be about 225°. Further, central axis 63 may cross or intersect with central axis 41 (e.g., for a given reference plane, as shown in the exemplary bottom elevation view of FIG. 2).

Figure 3:
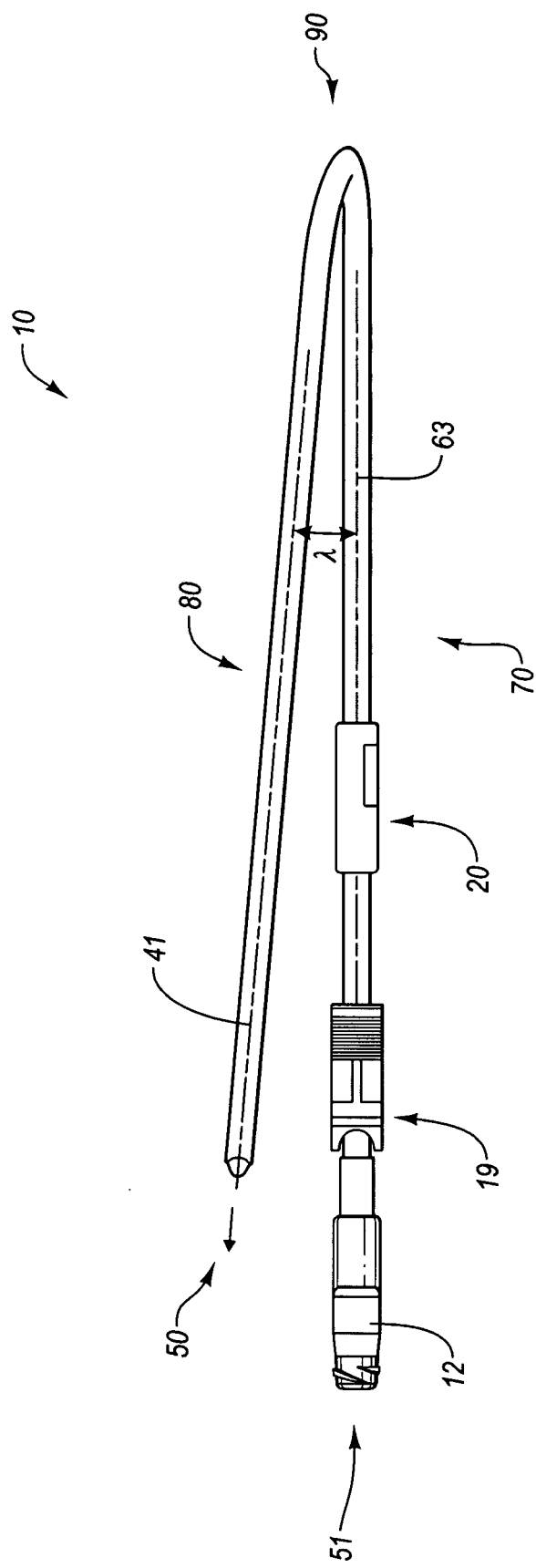
FIG. 3 shows a side view of the catheter shown in FIGS. 1 and 2.

In addition, the instant disclosure also contemplates that, optionally, an arcuate transition region of a catheter may form a separation angle between a first portion of a catheter and a second portion of a catheter that are connected by an arcuate transition region. More specifically, FIG. 3 shows a side view of the catheter 10 shown in FIGS. 1 and 2, wherein a separation angle $\lambda$ is formed generally between first portion 70 and second portion 80 of catheter 10. In one embodiment, separation angle $\lambda$ may be no more than about 90°. More specifically, separation angle $\lambda$ may be approximately 10° or less.

Figure 4:
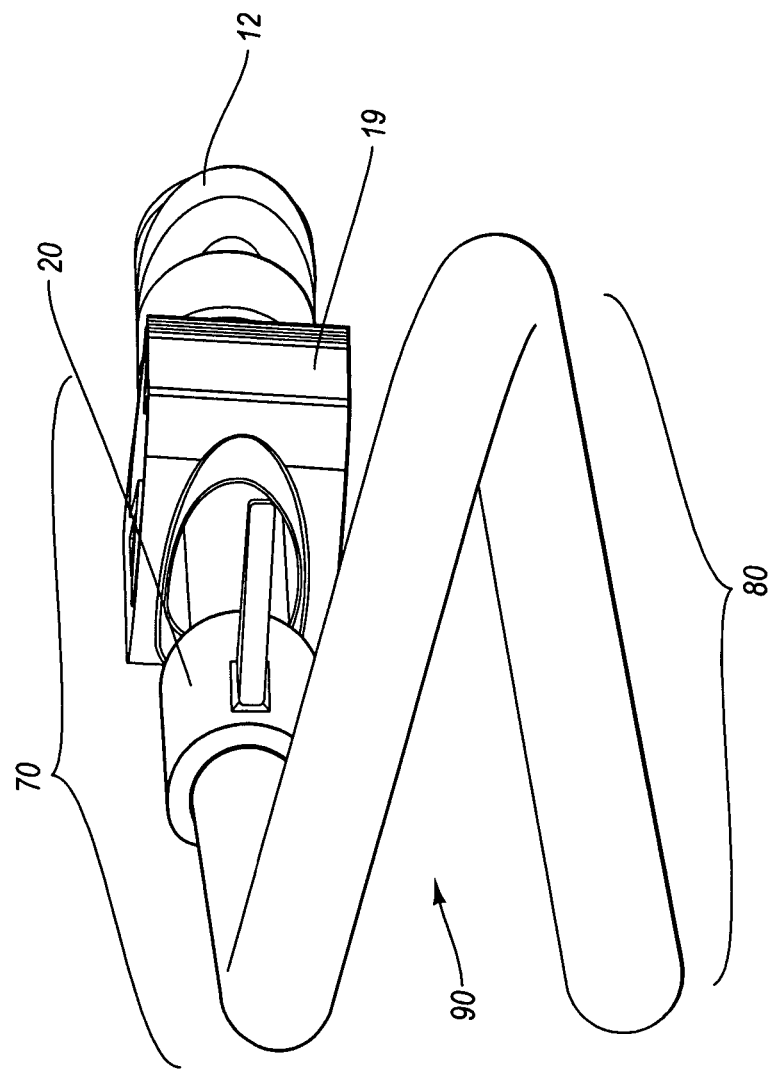
FIG. 4 shows a perspective view of the arcuate transition region of the catheter shown in FIGS. 1-3.

One of ordinary skill in the art will appreciate that a catheter including an arcuate transition region may include one or both of a selected exterior angle and a selected separation angle. Put another way, an exterior angle and a separation angle may be employed in combination or may be employed separately, without limitation. One of ordinary skill in the art will appreciate that, in one embodiment of a catheter comprising both a separation angle and an exterior angle, at least a portion of arcuate transition region 90 may be substantially helical. FIG. 4 shows a perspective view of arcuate transition region 90, wherein arcuate transition region 90 is substantially helical.

Such a configuration may provide a catheter that is more comfortable and easier to secure to a patient. Additionally or optionally, such a unique shape may act to stabilize the catheter within the tunnel/venotomy region and may prevent pistoning and migration of the catheter prior to tissue ingrowth. Since the transition or path from tunnel track into vein is generally three dimensional and tortuous in nature such a catheter including an arcuate transition region may contour more closely to this transition or path.

In further detail, an arcuate transition region may be capable of handling even relatively tight curves. For example, the catheter can be more easily "rolled" by the doctor prior to placement to adjust where the distal end will end up. As a further note, the catheter may comprise a material (e.g., polyurethane) that significantly softens at body temperature. Thus, in one embodiment, the shape of the catheter may not generate residual stresses (i.e., outward forces) exceeding forces generated by a conventional (e.g., U-shaped) catheters. Conventional catheters are disclosed in U.S. Pat. No. 5,509,897 to Twardowski et al.

In another embodiment, a catheter may comprise a catheter body extending between a distal end and a proximal end and defining a plurality of lumens. Further, the distal end may comprise a plurality of distal end regions that extend generally from a junction region of the catheter body. In addition, the proximal end may comprise a plurality of proximal extension legs. In general, the instant disclosure contemplates, as discussed above, that such a catheter may include an arcuate transition region extending between the first portion and the second portion of the catheter.

Figure 5:
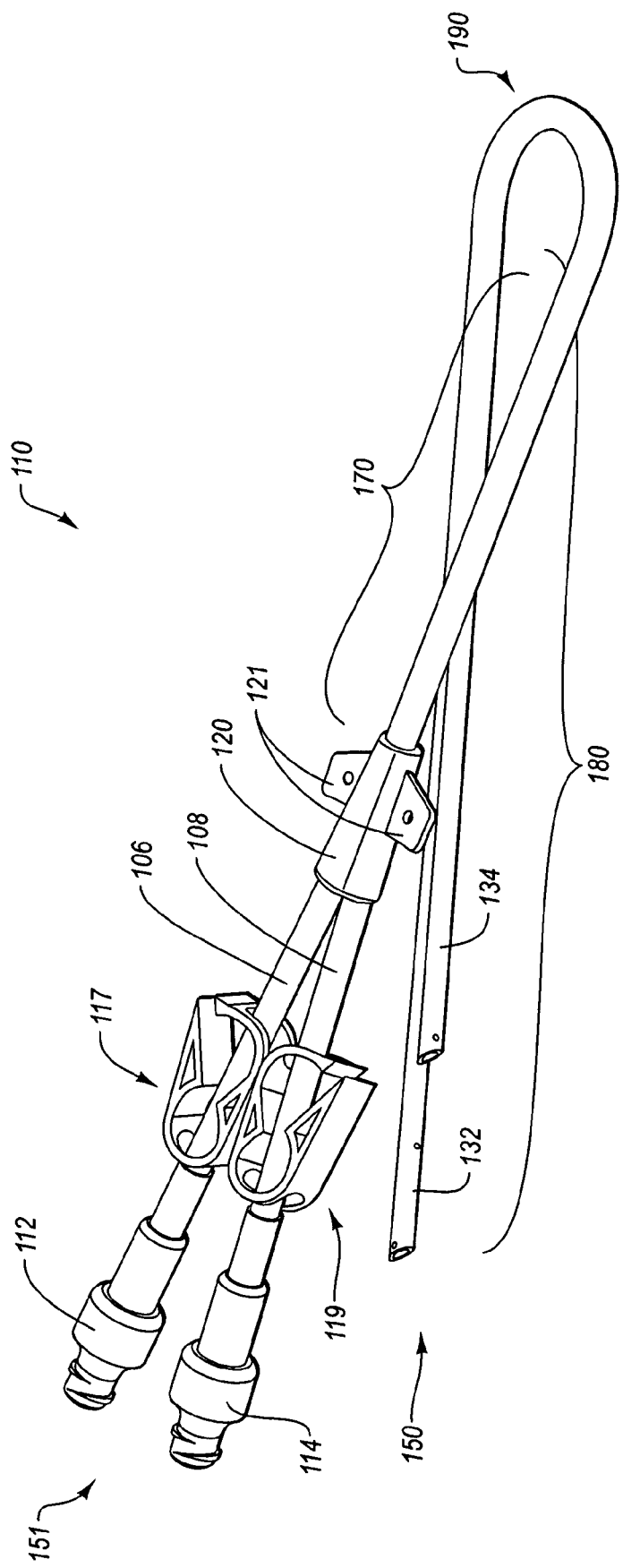
FIG. 5 shows another embodiment of a catheter including an arcuate transition region.
Figure 6:
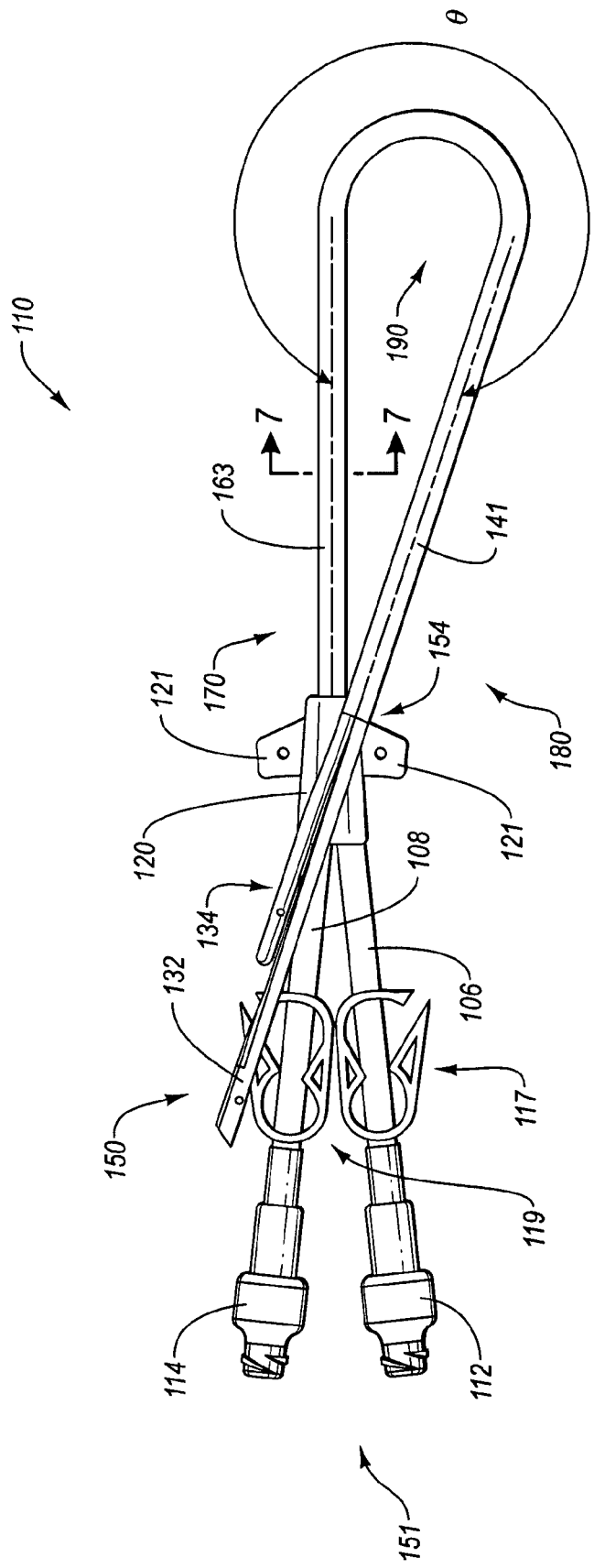
FIG. 6 shows a top elevation view of the catheter shown in FIG. 5.

For example, FIGS. 5 and 6 show a perspective view and a top elevation view, respectively, of a catheter 110 including distal end regions 132 and 134 (generally at a distal end 150 of the catheter 110) and proximal extension legs 108 and 106 (generally at a proximal end 151 of the catheter). Further, catheter 110 may include a proximal connection structure comprising a proximal end 151 of catheter 110. More particularly, couplings 112 and 114 may each comprise a luer-lock type coupling or other threaded or releasable fluid coupling structure as known in the art. As shown in FIG. 6, the hub structure 120 and proximal extension legs 108 and 106 may be suitably configured to establish a selected separation between the couplings 112 and 114 of proximal extension legs 108 and 106. Such a configuration may facilitate coupling of the catheter 110 to a fluid conveying or processing device, (e.g., dialysis equipment). As known in the art, hub structure 120 may facilitate fluid connection between proximal extension legs 108 and 106 and respective lumens defined by catheter 110. Further, the hub structure 120, as shown in FIGS. 5 and 6 may optionally include suture wings 121, which may be used to suture the catheter 110 to the patient for positioning of the catheter 110 after insertion into the patient.

Optionally, at least one of distal end regions 132 and 134 as well as one or more of proximal extension legs 108 and 106 and/or one or more of couplings 112 and 114, may include a visual or palpable indicator (e.g., a marking, a color, a symbol, a raised or indented feature, etc.) to indicate correspondence upon connection of catheter 110 to a fluid moving device. Also, each of proximal extension legs 108 and 106 may optionally include a clamp device, such as clamp devices 119 and 117, for clamping one or both of the proximal extension legs 108 and 106 when the catheter 110 is not connected to a fluid conveying device or when fluid flow through one or both of proximal extension legs 108 and 106 is not desired.

As shown in FIGS. 5 and 6, catheter 110 comprises a first portion 170, a second portion 180, and an arcuate transition region 190 extending between the first portion 170 and the second portion 180. Catheter 110 may comprise two lumens, wherein each of the lumens extends between one of proximal extension legs 106 or 108 and an associated one of distal end regions 132 or 134. More particularly, catheter 110 may include a first distal end region 132 and a second distal end region 134, each extending distally from a junction region 154. As shown in FIGS. 5 and 6, the second distal end region 134 may be shorter in length (e.g., measured from junction region 154) than a length (e.g., measured from junction region 154) of the first distal end region 132.

One of ordinary skill in the art will understand that proximal extension legs 106 and 108 in combination with couplings 112 and 114, respectively, may be used to connect catheter 110 to a fluid processing or fluid moving device (e.g., a medicine pump, a dialysis machine, etc.). Further, one of ordinary skill in the art will also understand that the first distal end region 132 may be used to remove fluid from a patient (e.g., as a venous extension leg in a hemodialysis application) and second distal end region 134 may be used to introduce fluid into a patient (e.g., as an arterial extension leg in a hemodialysis application). Additionally, the instant disclosure contemplates that the second distal end region 134 may be used to remove fluid from a patient (e.g., as a venous extension leg in a hemodialysis application) and first distal end region 132 may be used to introduce fluid into a patient (e.g., as an arterial extension leg in a hemodialysis application), if desired, without limitation.

The instant disclosure contemplates that arcuate transition region 190 may be configured, as discussed above in relation to any feature or aspect discussed above relative to arcuate transition region 90. Particularly, arcuate transition region 190 may be structured so that a first portion 170 is nonparallel with respect to a second portion 180.

FIG. 6 shows a top elevation view of catheter 110 that shows a selected exterior angle may be formed generally between the first portion 170 and the second portion 180, when the catheter 110 is in a substantially unstressed state. In one embodiment, an exterior angle formed between the first portion 170 and the second portion 180 may exceed 180°. In another embodiment, an exterior angle may be about 225°.

In one embodiment, an exterior angle formed between the first portion 170 and the second portion 180 may exceed 180°. For example, the angle formed between the first portion 170 and the second portion 180 may range from approximately 180-190°, 190-200°, 200-210°, 210-220°, 220-230°, 230-240°, 240-250°, 250-260°, and 260-270°. In yet another embodiment, an exterior angle formed between the first portion 170 and the second portion 180 may be less than 180°. For example, the angle formed between the first portion 170 and the second portion 180 may range from approximately 0-10°, 10-20°, 20-30°, 30-40°, 40-50°, 50-60°, 60-70°, 70-80°, 80-90°, 100-110°, 110-120°, 120-130°, 130-140°, 140-150°, 150-160°, 160-170°, and 170-180°. More particularly, an exterior angle between the first portion 170 and the second portion 180 may be about 225°. Further, one of ordinary skill in the art will appreciate that at least a portion of arcuate transition region 190 may comprise at least one of the following: a substantially circular arc, an elliptical arc, a parabolic curve, and a concave curve.

In addition, the instant disclosure generally contemplates, without limitation, that an exterior angle may be measured between any surfaces of the first portion 170 and/or the second portion 180, and such an exterior angle encompasses variations (i.e., increases or decreases) in the magnitude of the exterior angle due to a thickness or size of the first portion 170 and/or the second portion 180.

In one embodiment, an exterior angle may be measured between a central axis of the first portion 170 and a central axis of the second portion 180. For example, exterior angle $\theta$ is shown in FIG. 6 extending between a central axis 163 extending along first portion 170 (e.g., along a centroid of a cross-sectional area of the first portion 170) and a central axis 141 extending along the second portion 180 (e.g., along a centroid of a cross-sectional area of the second portion 180). Thus, a selected exterior angle θ may be formed between central axis 163 of first portion 170 and central axis 141 of second portion 180, when arcuate transition portion 190 is in a substantially unstressed state.

In one embodiment, exterior angle θ may exceed 180°. In another embodiment, exterior angle θ may be about 225°. Further, central axis 163 may cross or intersect with central axis 141 (e.g., for a given reference plane, as shown in the exemplary bottom elevation view of FIG. 6). In addition, arcuate transition region 190 of catheter 110 may form a separation angle (as discussed above relative to catheter 10) measured between first portion 170 and second portion 180 of catheter 110. In one embodiment, such a separation angle may be from approximately 0-90°. More particularly, a separation angle may be about 10° or less. Further, one of ordinary skill in the art will appreciate that a catheter including an arcuate transition region, in one embodiment, may comprise both a separation angle and an exterior angle. For example, in one embodiment, at least a portion of arcuate transition region 190 may be substantially helical.

Optionally, the first distal end region 132 may include one or more apertures formed through the first distal end region 132 in fluid communication with a lumen of catheter 110. Similarly, the second distal end region 134 may include one or more apertures in fluid communication with a lumen of catheter 110. Such one or more apertures formed through one or both first distal end region 132 and second distal end region 134 may facilitate fluid flow into or from the distal end regions 132 and 134.

Figure 7:
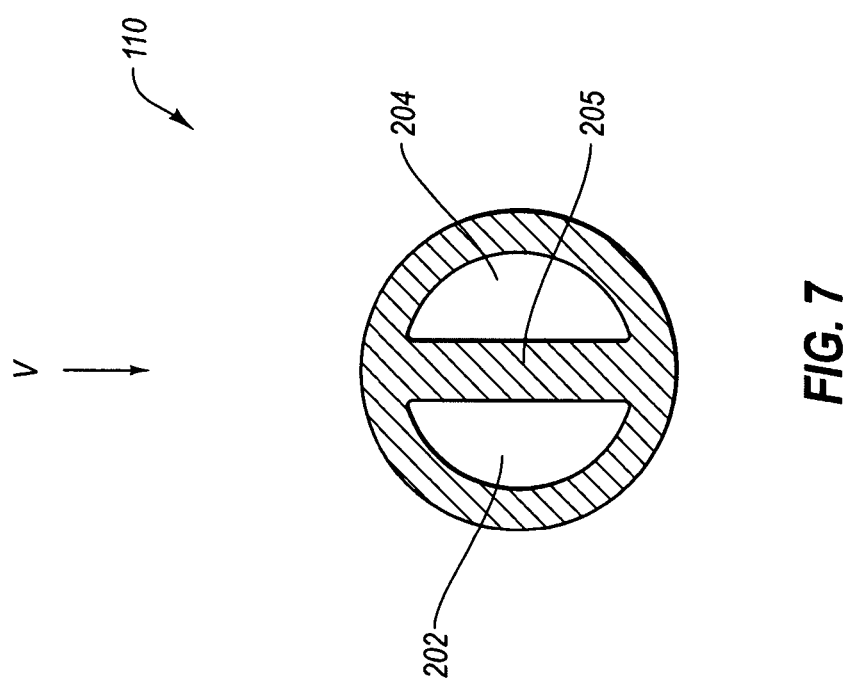
FIG. 7 shows a cross-sectional view of the catheter shown in FIGS. 5 and 6.

FIG. 7 shows a cross-sectional view of the catheter shown in FIG. 6, taken along reference line 7-7. Direction V, as shown in FIG. 7, denotes the direction from which catheter 110 is viewed in FIG. 6. As shown in FIG. 7, the portion of catheter 110 extending generally between hub structure 120 and junction region 154 may include two lumens, such as lumens 202 and 204, exhibiting a generally semicircular (e.g., a generally D-shaped) cross-sectional shape. In one embodiment, a septum 205 may comprise a membrane extending (e.g., diametrically) across a generally circular tube or lumen. In one embodiment, the cross-sectional shape shown in FIG. 7 may extend along catheter 110 substantially uniformly (i.e., substantially unchanging in orientation) along the length of catheter 110 between hub structure 120 and junction region 154. One of ordinary skill in the art will appreciate that the shape and cross-section configuration of any of the lumens of the catheter or extension legs may be varied, and, thus, the scope of the instant disclosure should not be limited to the above-described embodiments.

Figure 8:
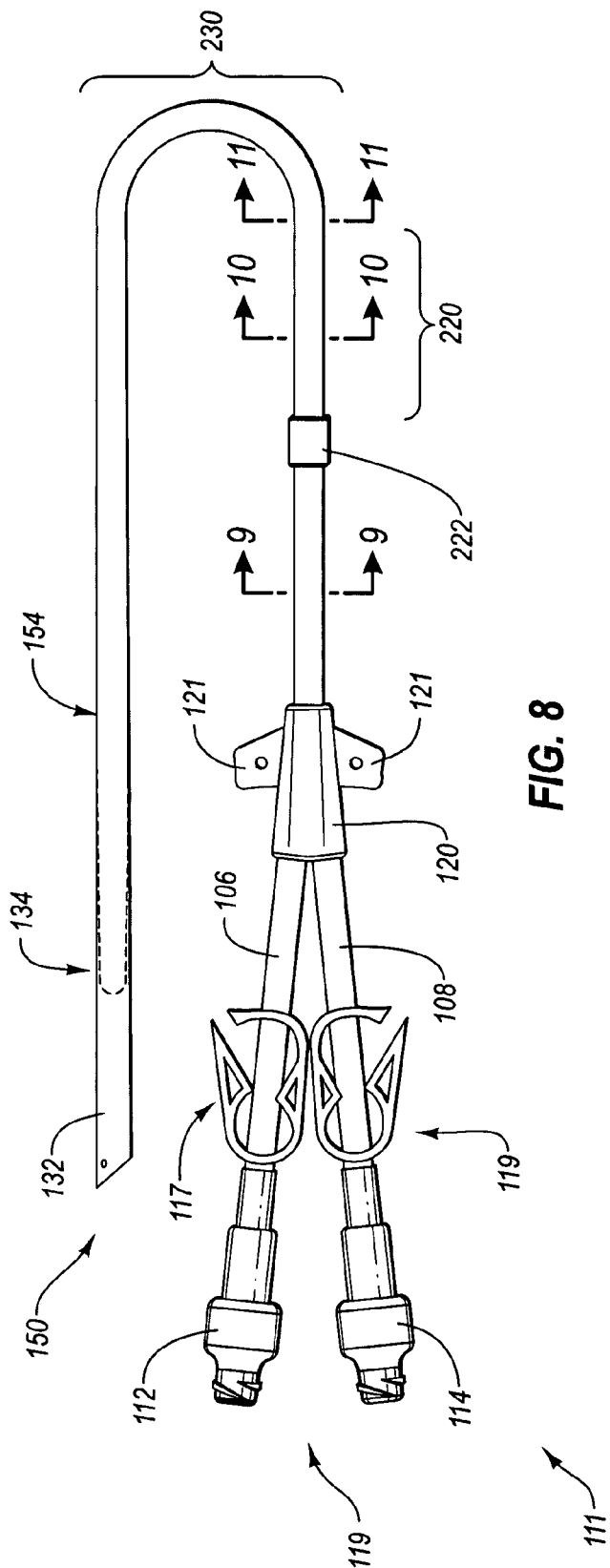
FIG. 8 shows a top elevation view of one embodiment of a catheter including at least one transformation region.

In another aspect of the instant disclosure, an orientation of a lumen may change along the length of at least a portion of a catheter. For example, a catheter may include at least one region within which an orientation of a lumen changes. Particularly, FIG. 8 shows a top elevation view of a catheter 111. In one embodiment, catheter 111, as shown in FIG. 8, may comprise a curved region 230. In other embodiments, catheter 111 may comprise an arcuate transition region as previously described, or may be substantially straight or linear, if desired. In addition, catheter 111 may include a proximal connection structure comprising a proximal end 151 including couplings 112 and 114 as described previously with respect to FIG. 6. Thus, hub structure 120 and extension legs 108 and 106 may be configured to establish a selected separation between the couplings 112 and 114 of proximal extension legs 108 and 106. Hub structure 120 may facilitate fluid connection between proximal extension legs 108 and 106 and respective lumens defined by catheter 111. Also, each of proximal extension legs 108 and 106 may optionally include a clamp device, such as clamp devices 119 and 117.

Figure 9:
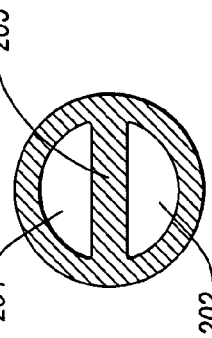
FIGS. 9-11 show different cross-sectional views of one embodiment of the catheter shown in FIG. 8.
Figure 10:
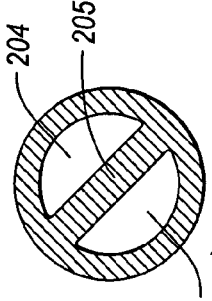
Figure 11:
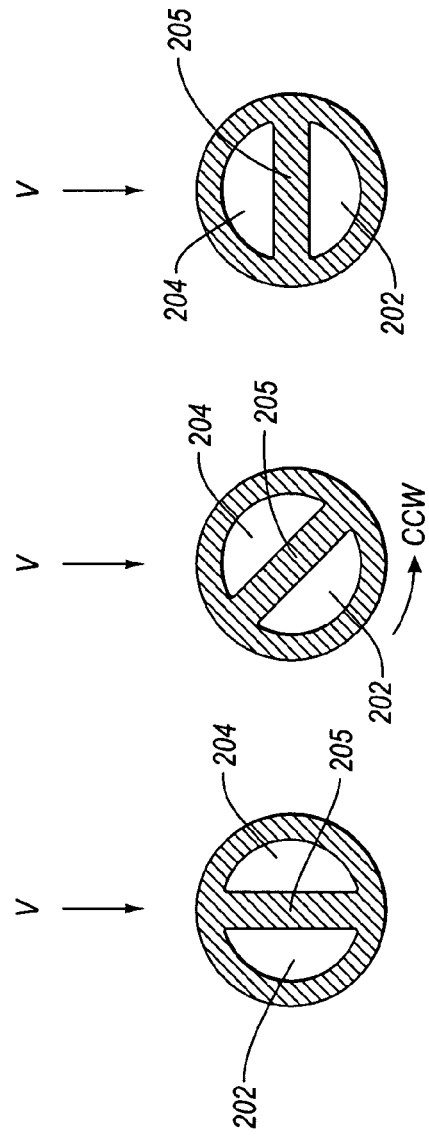

Further, catheter 111 may include a transformation region 220, within which an orientation of a lumen at least partially changes. More particularly, FIGS. 9-11 show cross-sectional views of catheter 111, taken at reference lines 9-9, 10-10, and 11-11, respectively. More specifically, FIGS. 9-11 show lumens 202 and 204 and septum 205. Direction V, as shown in FIGS. 9-11, denotes the direction from which catheter 111 is viewed in FIG. 8. In one embodiment, lumens 202 and 204, as shown in FIG. 8, may be generally unchanged between hub structure 120 and transformation region 220. Also, in one embodiment, lumens 202 and 204, as shown in FIG. 11, may be generally unchanged between transformation region 220 and junction region 154. As shown in FIG. 8, a coupler 222 may optionally operably connect transformation region 220 to an adjacent portion of catheter 111. Such a configuration may ease manufacturing of catheter 111.

Within transformation region 220, the orientation of lumens 202 and 204 may change between respective orientations shown in FIGS. 9 and 11. More specifically, as shown in FIG. 10, lumens 202 and 204 (and septum 205) may be rotated in a counter-clockwise (CCW) direction with reference to a distal direction along catheter 111 within transformation region 220. In other words, the position of the septum 205 may at least partially change within transformation region 220. In one embodiment, septum 205 may smoothly and continuously rotate along a distal direction within catheter 111, such as in a screw or twist transformation, wherein the angle of rotation is proportional to the distal translation at any position within transformation region 220. Lumens 202 and 204 as well as septum 205 may be otherwise transformed, abruptly or gradually, between the cross section shown in FIG. 9 and the cross section shown in FIG. 11, without limitation.

Figure 12:
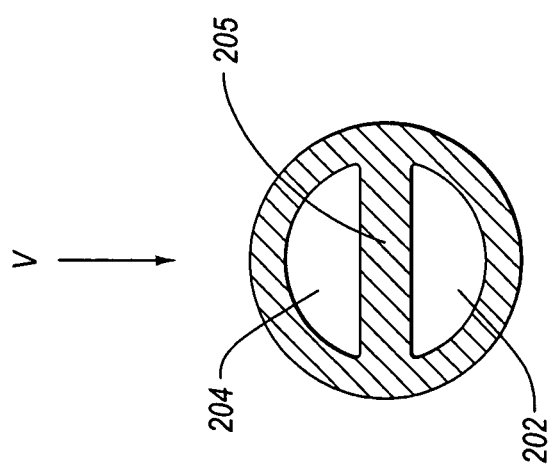
FIGS. 12 and 13 show different cross-sectional views of another embodiment of the catheter shown in FIG. 8.

In another embodiment, lumens 202 and 204, and septum 205, may rotate in a clockwise direction relative to a distal direction within transformation region 220 between the orientations shown in FIGS. 9 and 11. More specifically, as shown in FIG. 12, lumens 202 and 204, and septum 205, may be rotated in a clockwise direction (CW) with reference to a distal direction along catheter 111 within transformation region 220. In one embodiment, septum 205 may smoothly and continuously rotate along a distal direction within catheter 111, such as in a screw or twist transformation, wherein the angle of rotation is proportional to the distal translation at any position within transformation region 220. In one embodiment, the relative difference in the position of septum 205 shown in FIG. 9 and the position of septum 205 shown in FIG. 11 may be about 90°. In other embodiments, a difference in position of septum 205 may be any selected angle, such as an angle up to about 360°, or greater than 360°, without limitation.

Figure 13:
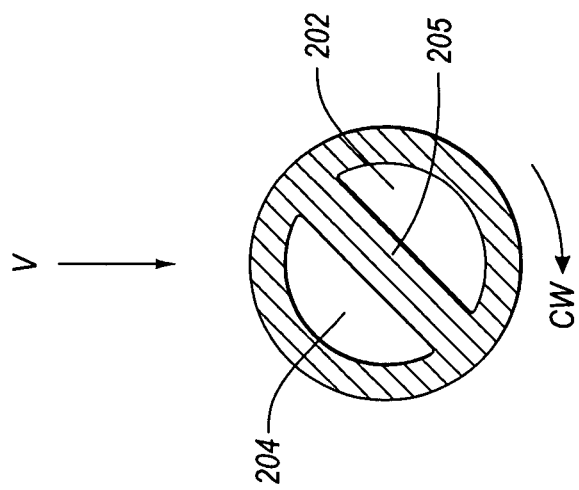

A catheter including at least one transformation region may exhibit at least one selected mechanical property (e.g., a flexibility, moment of inertia, strength, etc.). Also, one of ordinary skill in the art will appreciate that position of septum 205, as shown in FIG. 11 or FIG. 13, may be beneficial for resisting kinking and/or reducing the cross-sectional area of a selected region of the catheter. In one embodiment, septum 205 may be aligned with a plane of bending, such as a plane in which bending deflections occur. Thus, in one embodiment, a neutral axis of the septum during bending may lie within a cross-sectional area of the septum, similar to a web of an I-beam in pure bending. One of ordinary skill in the art will understand that in such a configuration, a moment of inertia of the septum may be generally maximized with respect to bending in the plane of bending. Thus, septum 205 may resist bending, and reduce deflection or deformation of the catheter 111, to a degree exceeding an identical septum oriented transverse to a plane of bending or otherwise oriented. Such a configuration may inhibit deformation of the catheter 111 and may resist deformation that causes one or more of lumens 202 and 204 to become smaller in cross-sectional area.

In a further embodiment, a catheter may include a plurality of transformation regions. For example, FIGS. 14-19 show a perspective view and several cross-sectional views of a catheter 101 including transformation regions 220 and 240. Generally, catheter 101 may be as described previously in relation to catheter 111. More particularly, within transformation region 220, lumens 202 and 204 may generally rotate clockwise, shown as CW in FIG. 16, between the orientation shown in FIG. 15 and the orientation shown in FIG. 17 (i.e., about 90°). In addition, catheter 101 further includes transformation region 240. As shown in FIGS. 18 and 19, lumens 202 and 204 of catheter 101 may generally rotate counter-clockwise, shown as CCW in FIG. 18, within region 240, between the orientation shown in FIG. 17 and the orientation shown in FIG. 19 (i.e., about 90°). Thus, proximal extension leg 106 may be in fluid communication with second distal end region 134 via lumen 202. Further, proximal extension leg 108 may be in fluid communication with first distal end region 132 via lumen 204. The instant disclosure contemplates that a catheter including at least one transformation region may include any lumen configuration, such as one or more lumens exhibiting a selected size and shape as known in the art, without limitation.

Figure 20:
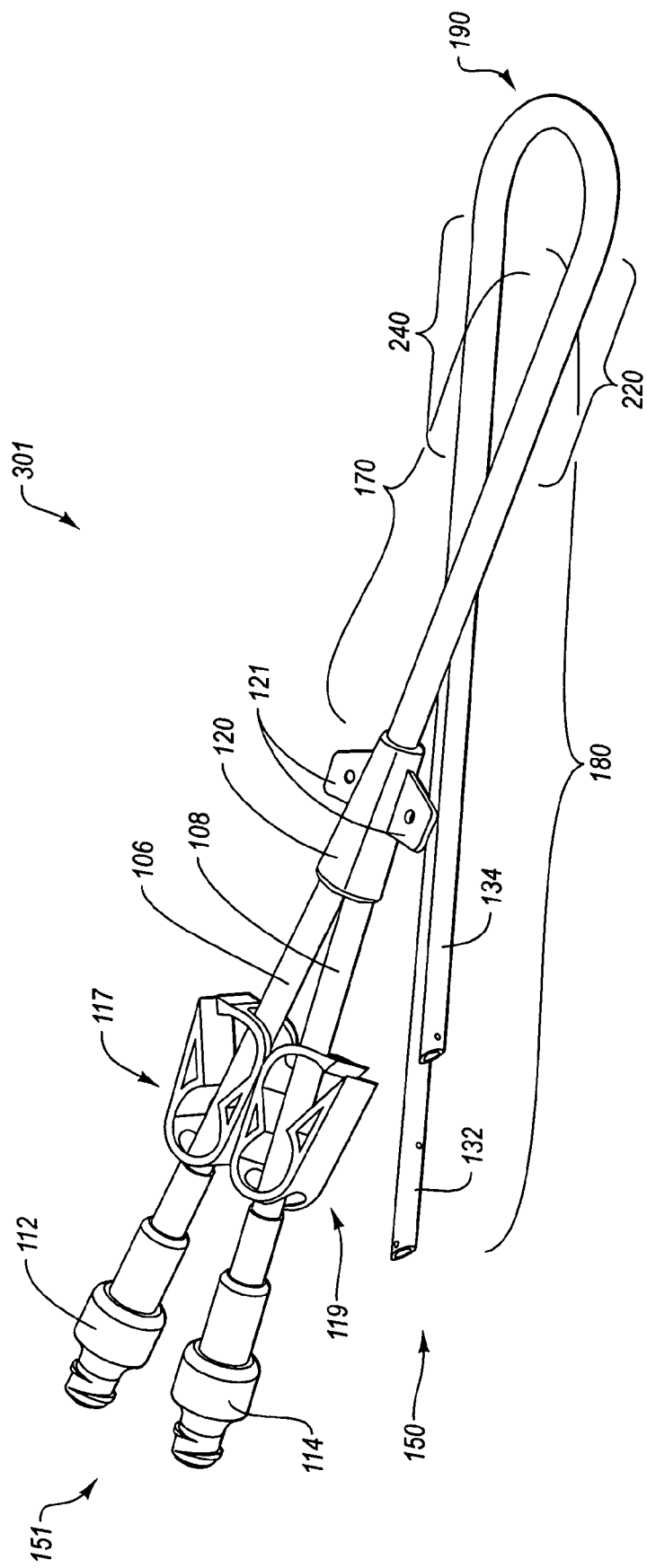
FIG. 20 shows one embodiment of a catheter including an arcuate transition region and at least one transformation region.
Figure 21:
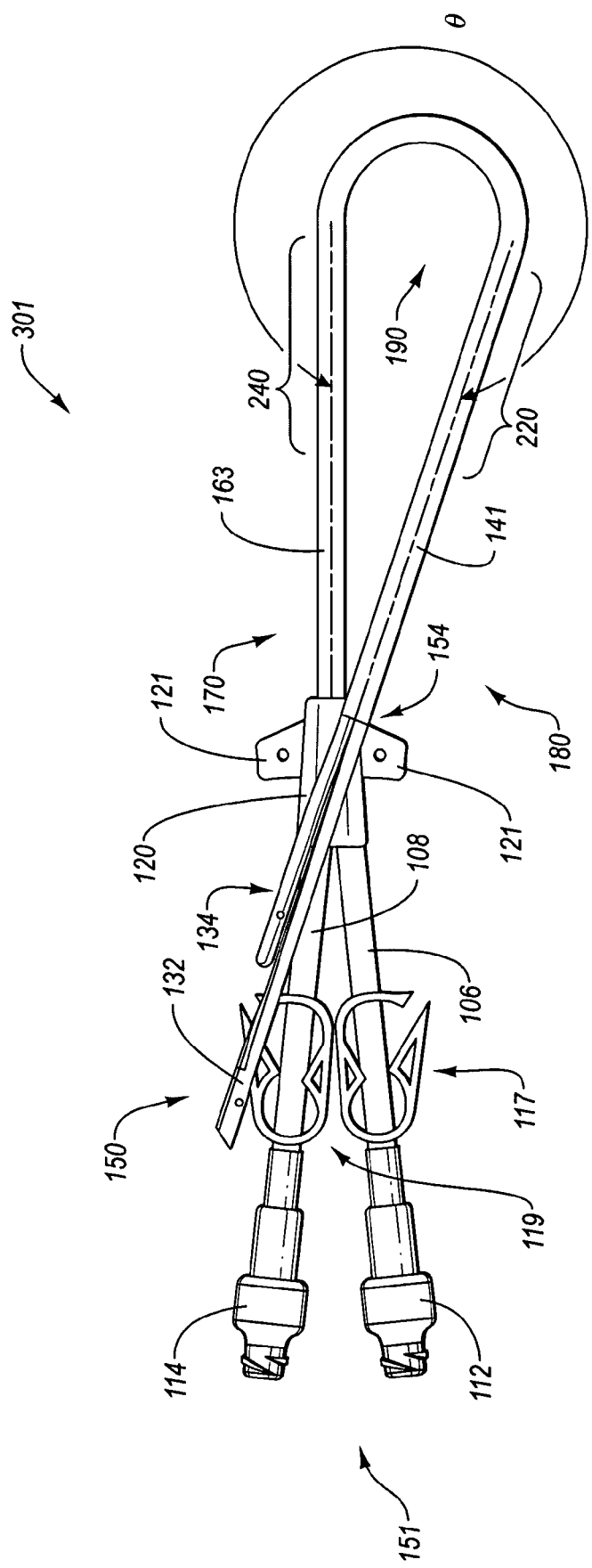
FIG. 21 shows a top elevation view of the catheter shown in FIG. 20.

The instant disclosure further encompasses any combination of features or attributes described above. For example, in one embodiment, a catheter may include an arcuate transition region and at least one transformation region. More particularly, FIGS. 20 and 21 show a perspective view and a top elevation view of catheter 301, which includes arcuate transition region 190 as well as transformation regions 220 and 240. In one embodiment, transformation region 220 may comprise lumens 202 and 204 as shown in FIGS. 15-17. More specifically, lumens 202 and 204 may rotate within transformation region 220 between the orientation shown in FIG. 15 and the orientation shown in FIG. 17 (e.g., about 90°). Further, in one embodiment, transformation region 240 may include lumens 202 and 204 as shown in FIGS. 17-19. Particularly, lumens 202 and 204 may rotate within transformation region 240 between the orientation shown in FIG. 17 and the orientation shown in FIG. 19 (e.g., about 90°). Accordingly, proximal extension leg 106 may be in fluid communication with second distal end region 134 via lumen 202 and proximal extension leg 108 may be in fluid communication with first distal end region 132 via lumen 204.

While aspects of the instant disclosure are described in relation to one embodiment of a catheter comprising two lumens, the instant disclosure is not so limited and other embodiments and catheter configurations are encompassed by the instant disclosure. For example, a catheter defining a plurality of lumens may comprise a plurality of substantially concentric tubes of varying diameter. In a further embodiment, a catheter may comprise three (or more) lumens. Generally, any lumen configuration known in the art may be utilized in combination with at least one of the following: an arcuate transition region and at least one transformation region. In addition, any distal tip structure as known in the art may comprise a catheter including at least one of the following: an arcuate transition region and at least one transformation region.

Figure 22:
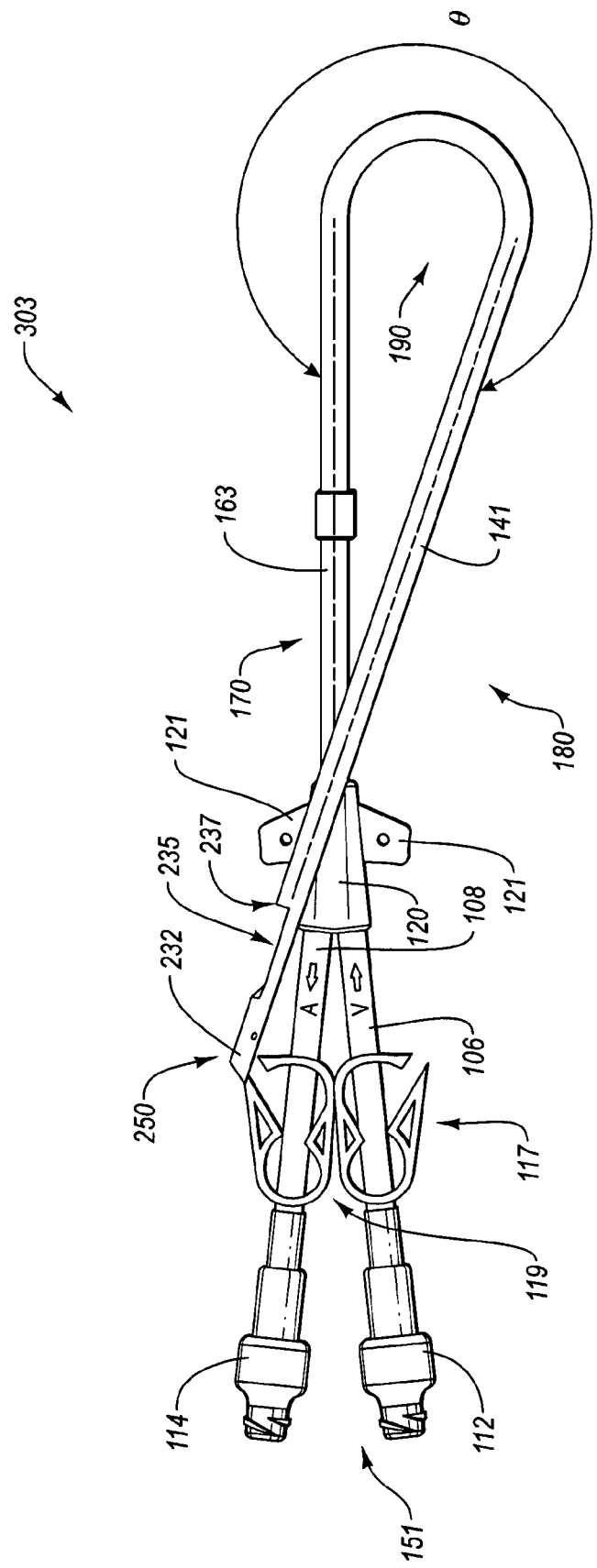
FIG. 22 shows a top elevation view of another embodiment of a catheter according to the instant disclosure.

For example, any distal tip structure, such as a so-called "stepped-tip," "split-tip," or any catheter distal tip structure as known in the art, without limitation, may be included by a catheter comprising at least one of the following: an arcuate transition region and at least one transformation region. For example, in one embodiment, a catheter may include a so-called "stepped tip." More particularly, FIG. 22 shows a catheter 303, which generally comprises components as described with respect to FIGS. 5 and 6. However, catheter 303 included a distal tip structure 250 including an extending end region 232 and a recessed region 235. As known in the art, an aperture 237 may be formed to communicate with at least one of the lumens of catheter 303. Thus, FIGS. 21 and 22 show respective catheters 301 and 303 comprising different distal tip configurations.

Figure 23:
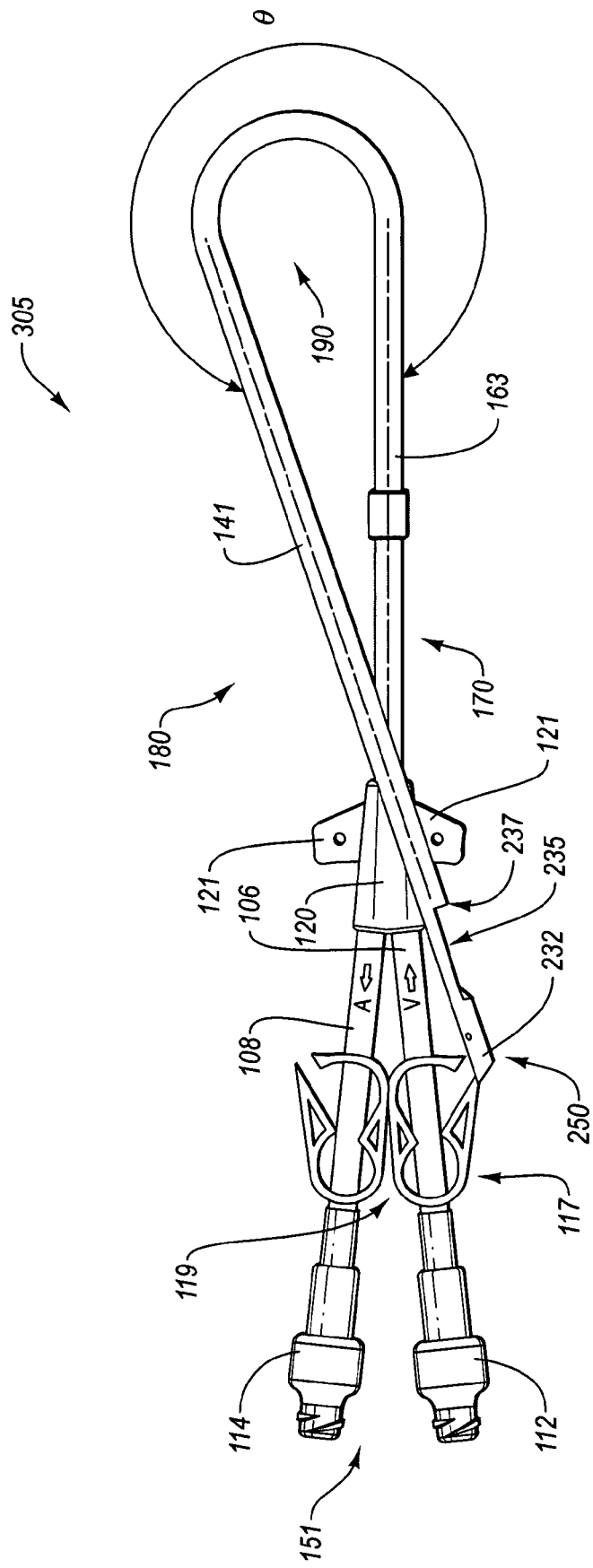
FIG. 23 shows a top elevation view of a further embodiment of a catheter according to the instant disclosure.

In a further aspect of the instant disclosure, one of ordinary skill in the art will appreciate that a transition region of a catheter may extend between a first portion and second portion of a catheter in a variety of ways. For instance, by way of illustration, FIG. 22 shows an arcuate transition region 190 extending from first portion 170, in a generally clockwise direction, toward second portion 180. In another embodiment, FIG. 23 shows a catheter 305, which generally comprises components as described with respect to FIG. 22, wherein an arcuate transition region 190 extends from first portion 170, in a generally counter-clockwise direction, toward second portion 180.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure described herein. In other words, various modifications and improvements of the embodiments specifically disclosed in the description above are within the scope of the appended claims.

The invention claimed is:

1. A catheter comprising:
   a catheter body extending between a distal end and a proximal end and defining at least one lumen, the catheter body including:
   a first straight portion, a second straight portion, and an arcuate transition region extending in a continuous helical curve for more than a half revolution between the first straight portion and the second straight portion, the first straight portion crossing the second straight portion for a given reference plane, the arcuate transition region positioned at or near an insertion site into a body of a patient during catheter use.

2. The catheter of claim 1, wherein the helical curve of the arcuate transition region traverses about 225°.

3. The catheter of claim 1, wherein a separation angle between 0° and 90° is formed between a central axis of the first portion and a central axis of the second portion.

4. The catheter of claim 1, wherein the catheter body defines at least two lumens.

5. The catheter of claim 4, wherein the distal end of the catheter body comprises a venous extension leg including a first lumen, and an arterial extension leg including a second lumen.

6. The catheter of claim 4, wherein the first straight portion and the second straight portion are separated by at least one transformation region within which a position of a septum dividing the at least two lumens at least partially changes.

7. The catheter of claim 6, wherein the position of the septum changes in a clockwise direction relative to a distal direction along the catheter.

8. The catheter of claim 6, wherein the position of the septum changes in a counter-clockwise direction relative to a distal direction along the catheter.

9. The catheter of claim 6, wherein the position of the septum changes up to about 360°.

10. The catheter of claim 1, wherein the proximal end of the catheter body comprises at least one connector.

11. The catheter of claim 10, wherein the proximal end of the catheter body comprises a first connector including a first lumen, and a second connector including a second lumen.

12. The catheter of claim 1, wherein at least a majority of the first straight portion is configured to be disposed outside the body of the patient and, wherein at least a segment of the second straight portion has a length suitable for insertion inside the body of the patient.

13. A catheter comprising:
a catheter body extending between a catheter body first end and a catheter body second end and defining two lumens in a Cartesian x-y-z coordinate system, the catheter body including:
a first portion extending from the catheter body second end along an x-axis in a positive direction to a first end of an arcuate transition region and a second portion extending from a second end of the arcuate transition region in a negative x and negative y direction to the catheter body first end, the arcuate transition region connecting the first portion to the second portion;
wherein, during use, at least a majority of the first portion is disposed outside of a body of a patient and, wherein at least a segment of the second portion has a length suitable for insertion inside the body of the patient; and
wherein an exterior arc angle between a central axis of the first portion and a central axis of the second portion is greater than 180° when the arcuate transition region is in a substantially unstressed state such that the first portion and the second portion have a common (x,y) coordinate point not at the catheter body first end or catheter body second end when a z axis of the x-y-z coordinate system is oriented parallel to a longitudinal axis of the arcuate transition region such that the arcuate transition region curls around the longitudinal axis.

14. The catheter of claim 13, wherein the catheter body first end includes a non-helical terminus.

15. The catheter of claim 13, wherein the first portion and the second portion are separated by at least one transformation region within which a position of a septum dividing the at least two lumens at least partially changes.

16. The catheter of claim 13, wherein a separation angle between 0° and 90° is formed between the central axis of the first portion and the central axis of the second portion in the z-direction.

17. The catheter of claim 13, wherein the exterior arc angle is about 225°.

* * * * *